United States Patent
Colpitts et al.

(10) Patent No.: US 7,282,207 B1
(45) Date of Patent: Oct. 16, 2007

(54) REAGENTS AND METHODS USEFUL FOR DETECTING DISEASES OF THE REPRODUCTIVE TISSUES

(75) Inventors: Tracey L. Colpitts, Round Lake, IL (US); John C. Russell, Pleasant Prairie, WI (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/549,342

(22) Filed: Apr. 13, 2000

Related U.S. Application Data

(63) Continuation-in-part of application No. 09/467,602, filed on Dec. 20, 1999, which is a continuation-in-part of application No. 09/215,818, filed on Dec. 18, 1998, and a continuation of application No. 09/016,387, filed on Jan. 30, 1998, which is a continuation-in-part of application No. 08/964,725, filed on Nov. 5, 1997, which is a continuation-in-part of application No. 08/912,276, filed on Aug. 15, 1997, and a continuation-in-part of application No. 08/912,149, filed on Aug. 15, 1997, now abandoned, which is a continuation-in-part of application No. 08/791,710, filed on Jan. 31, 1997, now abandoned, which is a continuation-in-part of application No. 08/744,211, filed on Nov. 5, 1996, now abandoned, which is a continuation-in-part of application No. 08/697,106, filed on Aug. 19, 1996, now abandoned, which is a continuation-in-part of application No. 08/697,105, filed on Aug. 19, 1996, now abandoned.

(51) Int. Cl.
*A61K 39/00* (2006.01)
*A61K 39/385* (2006.01)
*A61K 38/00* (2006.01)
*G01N 33/53* (2006.01)
*C07K 2/00* (2006.01)

(52) U.S. Cl. ................ 424/185.1; 424/184.1; 424/192.1; 424/193.1; 435/7.1; 530/300; 530/350; 530/388.1; 530/388.15; 530/389.1; 530/387.1; 530/387.7; 530/387.9

(58) Field of Classification Search ................ 530/300, 530/350, 388.1, 388.15, 389.1, 387.1, 387.7, 530/387.9; 424/185.1, 184.1, 192.1, 193.1; 435/7.1
See application file for complete search history.

(56) References Cited

U.S. PATENT DOCUMENTS

| 5,668,267 | A |   | 9/1997 | Watson et al. |
| 6,066,724 | A | * | 5/2000 | Ni et al. |
| 6,379,671 | B1 |  | 4/2002 | Colpitts |

FOREIGN PATENT DOCUMENTS

| WO | 9734997 | 9/1997 |
| WO | 9807857 | 2/1998 |
| WO | 9821331 | 5/1998 |
| WO | 0035950 | 6/2000 |

OTHER PUBLICATIONS

Amino acid database, Seq ID# 2,4 & 6 of U.S. Patent No. 6, 066, 724, 2000.*
T. E. Creighton et al., In: Proteins: Structures and Molecular Properties, Second Edition, pp. 78–102, New York, NY: W. H. Freeman and Co. 1993.
Friedman, P. et al. "BU101: A new breast specific uteroglobin." Anti Cancer Research, (Sep.–Oct., 1998) vol. 18 No. 5C, pp. 3840–3841—Meeting Info.: $22^{nd}$ International Breast Cancer Research Congress Of The International Association For Breast Cancer Research Athens, Greece Sep. 24–27, 1998: XP000929344.
Watson M. A. et al. "Mammaglobin, A Mammary–Specific Member of the Uteroglobin Gene Family, Is overexpressed in Human Breast Cancer"—Cancer Researdch, US, American Association for Cancer Research, Baltimore, MD, vol. 56, Feb. 15, 1996 pp. 860–865: XP002048615.

* cited by examiner

*Primary Examiner*—Alana M. Harris
(74) *Attorney, Agent, or Firm*—Cheryl L. Becker

(57) ABSTRACT

This invention relates generally to a multimeric polypeptide complex/antigen which may be utilized in detecting or diagnosing diseases of the uterus such as uterine cancer. Furthermore, the invention relates to methods and kits, for example, which utilize this antigen or an antibody thereto. The complex itself comprises at least one EU250 polypeptide and at least one polypeptide which may be a BU101 polypeptide and/or a TU104 polypeptide. The complex may further comprise other, as yet unknown, polypeptide sequences.

12 Claims, 2 Drawing Sheets

```
MAM            MKLLM VLMLAALSQH CYA.GSG...  ...CPLLENV ISKTINPQVS KTEYKELLQE
MAM B          MKLLM VLMLAALLLH CYA.DSG...  ...CKLLEDM VEKTINSDIS IPEYKELLQE
C3 Rat SBP     MKLVF LFLLVTIPIC CYASGSG...  ...CSILDEV IRGTINSTVT LHDYMKLVKP
BU101          MKLSV CLLLVTLALC CYQAN.....  AEFCPALVSE LLDFFFI..S EPLFKLSLAK
ESSBP I        MRLSV CLLMVSLALC CYQAH.....  ALVCPAVASE ITVFLFL..S DAAVNLQVAK
LIPOPHILIN A   MRLSV CLLLLTLALC CYRAN.....  AVVCQALGSE ITGFLLA..G KPVFKFQLAK
C1 Rat SBP     MSTIKLSL CLLIM.LAVC CYEAN....A SQICELVAHE TISFLMK..S EEELKKELEM
C2 Rat SBP     MRLSL CLLTI.LVVC CYEANGQTLA GQVCQALQDV TITFLLN..P EEELKRELEE
Cat 1a         MKGACVLVLL WAAL....LL ISGGN...:. CEICPAVKRD VDLFLTG..T PDEYVEQVAQ
Cat 1b         ML DAALPPCPTV AATAD..... CEICPAVKRD VDLFLTG..T PDEYVEQVAQ
CC10 MOUSE     MKIAI TITVVMLSIC CSSAS..... SDICPGFLQV LEALLME..S ESGYVASLKP
CC10 RAT       MKIAI TITVLMLSIC CSSAS..... SDICPGFLQV LEALLLG..S ESNYEAALKP
UTERO HARE     MKLTI TLALVTLALL CSPAS..... AGICPGFAHV IENLLLG..T PSSYETSLKE
UTERO RABBIT   MKLAI TLALVTLALL CSPAS..... AGICPRFAHV IENLLLG..T PSSYETSLKE
CC10 HUMAN     MKLAV TLTLVTLALC CSSAS..... AEICPSFQRV IETLLMD..T PSSYEAAMEL

FIDDNATTNA IDELKECF.L NQTDETLSNV EVFMQLIYDS SLCDLF
FIDSDAAAEA MGKFKQCF.L NQSHRTLKNF GLMMHTVYDS IWCNMKSN
YVQDHFTEKA VKQFKQCF.L DQTDKTLENV GVMMEAIFNS ESCQQPS
FDAPPEAVAA KLGVKRCTD. QMSLQKRSLI AEVLVKILKK ..CSV
LNPPPEALAA KLEVKHCTD. QISFKKRLSL EKVLVEIVKK ..CGV
FKAPLEAVAA KMEVKKCVD. TMAYEKRVLI TKTLGKIAEK ..CDR
YNAPPAAVEA KLEVKRCVD. QMSNGDRLVV AETLVYIFLE ..CGVKQWVE TYYPEIDFYY DMN
FDAPPEAVEA NLKVKRCIN. KIMYGDRLSM GTSLVFIMLK ..CDVKVWLQ INFPRGRWFS EIN
YKALPVVLEN ARILKNCVDA KMTEEDKENA LSVLDKIYTS PLC
YKALPVVLEN ARILKNCVDA KMTEEDKENA LSVLDKIYTS PLC
FNPGSDLQNA GTQLKRLVDT .LPQETRINI MKLTEKILTS PLCKQDLRF
FNPASDLQNA GTQLKRLVDT .LPQETRINI VKLTEKILTS PLCEQDLRV
FQPDDAMKDA GMQMKKVLDT .LPQTTRENI IKLTEKIVKS PLCM
FEPDDTMKDA GMQMKKVLDS .LPQTTRENI MKLTEKIVKS PLCM
FSPDQDMREA GAQLKKLVDT .LPQKPRESI IKLMEKIAQS SLCN
```

FIG. 1 q13296 MAMMAGLOBIN
o75556 EU250
p02780 RAT PROSTATEIN, C3
q06318 CLARA CELL 10kD PROTEIN, MOUSE
p17559 CLARA CELL 10kD PROTEIN, RAT
p06913 UTEROGLOBIN, HARE
p02779 UTEROGLOBIN, RABBIT
p11684 CLARA CELL 10kD PROTEIN, HUMAN
p30438 CAT MAJOR ALLERGEN, 1a
p30439 CAT MAJOR ALLERGEN, 1b
p02782 RAT PROSTATEIN, C1
p02781 RAT PROSTATEIN, C2
p95968 LIPOPHILIN A
w54271 BU101
w35802 TU104

SEQUENCE LISTING

<160> NUMBER OF SEQ ID NOS: 12

<210> SEQ ID NO 1
<211> LENGTH: 482
<212> TYPE: DNA
<213> ORGANISM: Homo sapiens

<400> SEQUENCE: 1

```
aaatagccct gggctctgca gctccacagg ctcctggggt ggagtccaaa tcactcattg    60
tttgtgaaag ctgagctcac agcaaaacaa gccaccatga agctgtcggt gtgtctcctg   120
ctggtcacgc tggccctctg ctgctaccag gccaatgccg agttctgccc agctcttgtt   180
tctgagctgt tagacttctt cttcattagt gaacctctgt tcaagttaag tcttgccaaa   240
tttgatgccc ctccggaagc tgttgcagcc aagttaggag tgaagagatg cacggatcag   300
atgtcccttc agaaacgaag cctcattgcg gaagtcctgg tgaaaatatt gaagaaatgt   360
agtgtgtgac atgtaaaaac tttcatcctg gtttccactg tctttcaatg cacccctgat   420
cttcactgca gaatgtaaag gtttcaacgt cttgctttaa taaatcactt gctctccacg   480
tc                                                                   482
```

<210> SEQ ID NO 2
<211> LENGTH: 90
<212> TYPE: PRT
<213> ORGANISM: Homo sapiens

<400> SEQUENCE: 2

```
Met Lys Leu Ser Val Cys Leu Leu Val Thr Leu Ala Leu Cys Cys
 1               5                  10                  15

Tyr Gln Ala Asn Ala Glu Phe Cys Pro Ala Leu Val Ser Glu Leu Leu
                20                  25                  30

Asp Phe Phe Phe Ile Ser Glu Pro Leu Phe Lys Leu Ser Leu Ala Lys
            35                  40                  45

Phe Asp Ala Pro Pro Glu Ala Val Ala Ala Lys Leu Gly Val Lys Arg
        50                  55                  60

Cys Thr Asp Gln Met Ser Leu Gln Lys Arg Ser Leu Ile Ala Glu Val
    65                  70                  75                  80

Leu Val Lys Ile Leu Lys Lys Cys Ser Val
                85                  90
```

<210> SEQ ID NO 3
<211> LENGTH: 95
<212> TYPE: PRT
<213> ORGANISM: Homo sapiens

<400> SEQUENCE: 3

```
Met Lys Leu Leu Met Val Leu Met Leu Ala Ala Leu Leu Leu His Cys
 1               5                  10                  15

Tyr Ala Asp Ser Gly Cys Lys Leu Leu Glu Asp Met Val Glu Lys Thr
                20                  25                  30

Ile Asn Ser Asp Ile Ser Ile Pro Glu Tyr Lys Glu Leu Leu Gln Glu
            35                  40                  45

Phe Ile Asp Ser Asp Ala Ala Ala Glu Ala Met Gly Lys Phe Lys Gln
        50                  55                  60

Cys Phe Leu Asn Gln Ser His Arg Thr Leu Lys Asn Phe Gly Leu Met
    65                  70                  75                  80

Met His Thr Val Tyr Asp Ser Ile Trp Cys Asn Met Lys Ser Asn
                85                  90                  95
```

<210> SEQ ID NO 4
<211> LENGTH: 508
<212> TYPE: DNA
<213> ORGANISM: Homo sapiens

<400> SEQUENCE: 4

```
ctgccacgca cgactgaaca cagacagcag ccgcctcgcc atgaagctgc tgatggtcct    60
```

-continued

```
catgctggcg gccctcctcc tgcactgcta tgcagattct ggctgcaaac tcctggagga      120
catggttgaa aagaccatca attccgacat atctatacct gaatacaaag agcttcttca      180
agagttcata gacagtgatg ccgctgcaga ggctatgggg aaattcaagc agtgtttcct      240
caaccagtca catagaactc tgaaaaactt tggactgatg atgcatacag tgtacgacag      300
catttggtgt aatatgaaga gtaattaact ttacccaagg cgtttkgctc agagggctac      360
agactatggc cagaactcat ctgttgattg ctagaaacca cttttctttc ttgtgttgtc      420
tttttatgtg gaaactgcta gacaactgtt gaaacctcaa attcatttcc atttcaataa      480
actaactgca aatcactaga aaaaaaa                                          508
```

<210> SEQ ID NO 5
<211> LENGTH: 381
<212> TYPE: DNA
<213> ORGANISM: Homo sapiens

<400> SEQUENCE: 5

```
ggtcgaatcc aaatcactca ttgtgaaagc tgagctcaca gccgaataag ccaccatgag       60
gctgtcagtg tgtctcctga tggtctcgct ggcccttttgc tgctaccagg cccatgctct      120
tgtctgccca gctgttgctt ctgagatcac agtcttctta ttcttaagtg acgctgcggt      180
aaacctccaa gttgccaaac ttaatccacc tccagaagct cttgcagcca agttggaagt      240
gaagcactgc accgatcaga tatcttttaa ggaacggctc tcattgaaaa agtcctgggt      300
gggaatagtg aaaaaatgtg gtgtgtgaca tgtaaaaatg ctcaacctgg gtttcmaarg      360
tcttttcaac ggcaacctga t                                                381
```

<210> SEQ ID NO 6
<211> LENGTH: 508
<212> TYPE: DNA
<213> ORGANISM: Homo sapiens

<400> SEQUENCE: 6

```
gggcaagtgg aaccactggc ttggtggatt ttgctagatt tttctgattt ttaaactcct       60
gaaaaatatc ccagataact gtcatgaagc tggtaactat cttcctgctg gtgaccatca      120
gcctttgtag ttactctgct actgccttcc tcatcaacaa agtgcccctt cctgttgaca      180
agttggcacc tttacctctg acaacattc ttcccttttat ggatccatta aagcttcttc      240
tgaaaactct gggcatttct gttgagcacc ttgtggaggg gctaaggaag tgtgtaaatg      300
agctgggacc agaggcttct gaagctgtga agaaactgct ggaggcgcta tcacacttgg      360
tgtgacatca agataaagag cggaggtgga tggggatgga agatgatgct cctatcctcc      420
ctgcctgaaa cctgttctac caattataga tcaaatgccc taaaatgtag tgacccgtga      480
aaaggacaaa taaagcaatg aatacatt                                         508
```

<210> SEQ ID NO 7
<211> LENGTH: 93
<212> TYPE: PRT
<213> ORGANISM: Homo sapiens

<400> SEQUENCE: 7

```
Met Lys Leu Val Thr Ile Phe Leu Leu Val Thr Ile Ser Leu Cys Ser
  1               5                  10                  15

Tyr Ser Ala Thr Ala Phe Leu Ile Asn Lys Val Pro Leu Pro Val Asp
             20                  25                  30
```

-continued

Lys Leu Ala Pro Leu Pro Leu Asp Asn Ile Leu Pro Phe Met Asp Pro
            35                  40                  45

Leu Lys Leu Leu Leu Lys Thr Leu Gly Ile Ser Val Glu His Leu Val
 50                  55                  60

Glu Gly Leu Arg Lys Cys Val Asn Glu Leu Gly Pro Glu Ala Ser Glu
 65                  70                  75                  80

Ala Val Lys Lys Leu Leu Glu Ala Leu Ser His Leu Val
                85                  90

<210> SEQ ID NO 8
<211> LENGTH: 562
<212> TYPE: DNA
<213> ORGANISM: Homo sapiens
<220> FEATURE:
<221> NAME/KEY: misc_feature
<222> LOCATION: (17)...(17)
<223> OTHER INFORMATION: n = a or g or c or t/u, unknown or other at
      position 17

<400> SEQUENCE: 8
gcagggcttt ctcaggngcg cgggcgaggc cggcgctgga ggggcgagga ccgggtataa      60
gaagcctcgt ggccttgccc gggcagccgc aggttccccg cgcgccccga gccccgcgc     120 catgaagctc gccgccctcc tggggctctg cgtggccctg tcctgcagct ccgctgytgc     180
tttcttagtg ggctcggcca agcctgtggc ccagcctgtc gctgcgctgg agtcggcggc     240
ggaggccggg gccgggaccc tggccaaccc cctcggcacc ctcaacccgc tgaagctcct     300
gctgagcagc ctgggcatcc ccgtgaacca cctcatagag ggctcccaga agtgtgtggc     360
tgagctgggt ccccaggccg tgggggccgt gaaggccctg aaggccctgc tggggccct     420 gacagtgttt ggctgagccg agactggagc atctacacct gaggacaaga cgctgcccac     480
ccgcgagggc tgaaaacccc gccgcgggga ggaccgtcca tccccttccc ccggcccctc     540
tcaataaacg tggttaagag ca                                              562

<210> SEQ ID NO 9
<211> LENGTH: 104
<212> TYPE: PRT
<213> ORGANISM: Homo sapiens

<400> SEQUENCE: 9

Met Lys Leu Ala Ala Leu Leu Gly Leu Cys Val Ala Leu Ser Cys Ser
 1               5                  10                  15

Ser Ala Val Ala Phe Leu Val Gly Ser Ala Lys Pro Val Ala Gln Pro
                20                  25                  30

Val Ala Ala Leu Glu Ser Ala Ala Glu Ala Gly Ala Gly Thr Leu Ala
            35                  40                  45

Asn Pro Leu Gly Thr Leu Asn Pro Leu Lys Leu Leu Leu Ser Ser Leu
 50                  55                  60

Gly Ile Pro Val Asn His Leu Ile Glu Gly Ser Gln Lys Cys Val Ala
 65                  70                  75                  80

Glu Leu Gly Pro Gln Ala Val Gly Ala Val Lys Ala Leu Lys Ala Leu
                85                  90                  95

Leu Gly Ala Leu Thr Val Phe Gly
            100

<210> SEQ ID NO 10
<211> LENGTH: 90
<212> TYPE: PRT
<213> ORGANISM: Homo sapiens

```
<400> SEQUENCE: 10

Met Arg Leu Ser Val Cys Leu Leu Met Val Ser Leu Ala Leu Cys Cys
1               5                   10                  15

Tyr Gln Ala His Ala Leu Val Cys Pro Ala Val Ala Ser Glu Ile Thr
            20                  25                  30

Val Phe Leu Phe Leu Ser Asp Ala Ala Val Asn Leu Gln Val Ala Lys
        35                  40                  45

Leu Asn Pro Pro Glu Ala Leu Ala Ala Lys Leu Glu Val Lys His
    50                  55                  60

Cys Thr Asp Gln Ile Ser Phe Lys Glu Arg Leu Ser Leu Lys Lys Ser
65                  70                  75                  80

Trp Val Gly Ile Val Lys Lys Cys Gly Val
                85                  90

<210> SEQ ID NO 11
<211> LENGTH: 68
<212> TYPE: DNA
<213> ORGANISM: Artificial Sequence
<220> FEATURE:
<223> OTHER INFORMATION: Restriction site

<400> SEQUENCE: 11
agctcggaat tccgagcttg gatcctctag agcggccgcc gactagtgag ctcgtcgacc      60
cgggaatt                                                               68

<210> SEQ ID NO 12
<211> LENGTH: 68
<212> TYPE: DNA
<213> ORGANISM: Artificial Sequence
<220> FEATURE:
<223> OTHER INFORMATION: Restriction site

<400> SEQUENCE: 12
aattaattcc cgggtcgacg agctcactag tcggcggccg ctctagagga tccaagctcg      60
gaattccg                                                               68
```

REAGENTS AND METHODS USEFUL FOR DETECTING DISEASES OF THE REPRODUCTIVE TISSUES

CROSS-REFERENCE TO RELATED APPLICATIONS

This application is a continuation-in-part of pending U.S. patent application Ser. No. 09/467,602 filed on Dec. 20, 1999, which is a continuation-in-part of allowed U.S. patent application Ser. No. 09/215,818 filed on Dec. 18, 1998, which is a continuation-in-part of 1) U.S. Pat. No. 6,183, 952, issued on Feb. 6, 2001, which is a continuation-in-part of U.S. patent application Ser. No. 08/697,105, filed on Aug. 19, 1996, now abandoned, as well as 2) a continuation-in-part of U.S. patent application Ser. No. 08/912,149, filed on Aug. 15, 1997 now abandoned, which is a continuation-in-part of U.S. application Ser. No. 08/697,106, filed on Aug. 19, 1996, now abandoned which is a continuation-in part of Ser. No. 08/912,276 filed Aug. 15, 1997 from which priority is claimed pursuant to 35 U.S.C. § 120 and which are all incorporated herein by reference in their entity. Furthermore, the subject application is also a continuation-in-part of 1) pending U.S. patent application Ser. No. 08/964,725 filed on Nov. 5, 1997 which is a continuation-in-part of abandoned U.S. patent application Ser. No. 08/744,211 filed on Nov. 5, 1996 and 2) pending U.S. patent application Ser. No. 09/016, 387 filed on Jan. 30, 1998 which is continuation-in-part of abandoned U.S. patent application Ser. No. 08/791,710 filed on Jan. 31, 1997. All patent applications and issued patents, cited above, are hereby incorporated in their entirety, by reference.

BACKGROUND OF THE INVENTION

Background Information

Cancer of the uterus is the most common cancer of the female reproductive tract and the fourth most common cancer among women in the United States. About 35,000 new cases of endometrial cancer are diagnosed in the United States each year. In 2000, an estimated 6500 women will die of the disease (American Cancer Society statistics). The racial and ethnic diversity of endometrial cancer follows a pattern similar to that of breast cancer. Women with the highest age-adjusted incidence of endometrial cancer in the SEER areas include Hawaiians, whites, Japanese, and blacks. The lowest rates occur among Korean, Vietnamese, and American Indian women.

The most common type of cancer of the uterus develops in the glandular cells or endometrium, the lining inside of the uterine cavity. This is the same tissue that is shed each month during a normal menstrual period. This type of cancer is called endometrial or uterine cancer. A small number of endometrial cancers (3%) are sarcomas, which grow in the muscular and connective tissue elements of the uterus. As uterine cancer grows, it may invade nearby organs. Uterine cancer cells also may break away from the tumor and spread to other parts of the body, such as the lungs, liver, and bones.

Currently, there are no screening tests for uterine cancer which are recommended on a routine basis other than yearly pelvic examination. The focus in this cancer is on prevention by avoiding excessive estrogenic stimulation of the uterine lining due to obesity, hormone replacement or other factors (National Comprehensive Cancer Network). If a patient is found with local disease (cancer confined entirely to the uterus), the five-year survival rate is observed to be 95%. As the disease progresses to regional (malignant cancer that has extended beyond the limits of the uterus directly into surrounding organs, tissues, or lymph nodes), the five-year survival rate decreases to 64%. If the disease is found to be distant (malignant cancer that has spread to parts of the body remote from the uterus), the five-year survival rate is lowest at only 25% (American Cancer Society, Surveillance Research).

The most common symptom of uterine cancer is abnormal vaginal bleeding, especially after menopause. Other symptoms include difficult or painful urination, pain during intercourse, or pain in the pelvic area. These symptoms are not diagnostic for cancer however, and further examination is necessary. Follow-up with a physician may involve a pelvic exam, a pap test, or a biopsy. A biopsy is necessary for diagnosis. No tumor markers for uterine cancer are known to date. Diagnosis is made by an H&E stain of the biopsy specimen. As has been shown with other cancers, diagnosis by histology is not as sensitive as diagnosis using tumor markers, either by immunohistochemical techniques, molecular techniques, or immunoassay. Improvement in the detection, diagnosis, staging, monitoring, and prognostication of uterine cancer can improve the survival rate of the patient.

The choice of treatment depends on the size of the tumor, the stage of the disease, whether female hormones affect tumor growth, and tumor grade. The tumor grade tells how closely the cancer resembles normal cells and suggests how fast the cancer is likely to grow. Low-grade cancers are likely to grow and spread more slowly than high-grade cancers.

Most women with uterine cancer are treated with surgery. Some have radiation therapy. A smaller number of women may be treated with hormone therapy or chemotherapy. Surgery to remove the uterus (hysterectomy) and the fallopian tubes and ovaries (bilateral salpingo-oophorectomy) is the treatment recommended for most women with uterine cancer. It is important to remove the ovaries during surgery because this represents one area where endometrial cancer may spread. Often, involvement of the ovaries with endometrial cancer cannot be observed by casual inspection during surgery and will only become apparent after removal when the pathologist looks at them under the microscope. Lymph nodes from the pelvic and lower aortic areas may also be removed during surgery to look for spread of the cancer, since this is the most common route of spread. If cancer has reached the lymph nodes, it may mean that the disease has spread to other parts of the body. If cancer cells have not spread beyond the endometrium, the disease can usually be cured with surgery alone.

After hysterectomy, additional treatment with radiation and/or chemotherapy is required in only a minority of cases in which spread of disease outside the uterus has been found or is suspected. Radiation therapy may be applied with an implant placed directly is into or near the tumor site (internal radiation) or be applied externally. Radiation therapy may be used in addition to surgery to treat women with certain stages of uterine cancer. Radiation may be used before surgery to shrink the tumor or after surgery to destroy any cancer cells that remain in the area.

Hormone therapy may be given to women who are unable to have surgery. This form of treatment is often recommended for women who have metastatic or recurrent endometrial cancer. Chemotherapy is also an option for patients with uterine cancer that has spread. Accurate staging and prognostication of the disease is critical to choosing optimal therapy.

Known risk factors include age (cancer of the uterus is most common in women over age 50); endometrial hyperplasia (women who have endometrial hyperplasia have a higher risk of developing uterine cancer); estrogen replacement therapy (women who use ERT to control symptoms associated with menopause, to prevent osteoporosis or to reduce the risk of heart disease or stroke may have an increased risk of uterine cancer. Long-term treatment and large doses seem to increase this risk. Using a combination of estrogen and progesterone decreases the risk linked to the use of estrogen alone. The progesterone protects the endometrium from the cancer-causing effect of estrogen); obesity (fat converts certain hormones into a form of estrogen. Women with excess fat produce higher levels of estrogen); diabetes and high blood pressure; and tamoxifen (an increased risk of developing uterine cancer has been found in women taking tamoxifen for the treatment of breast cancer. This risk may be related to the estrogen-like effect of this drug on the uterus). Other risk factors for uterine cancer are also related to estrogen, including having few or no children or entering menopause late in life. Some studies of women who have used oral contraceptives that combine estrogen and progesterone show that these women have a lower than average risk of uterine cancer.

The key risk factor for uterine cancer is estrogen, a hormone that occurs naturally in all women. Prevention of the disease by elimination of estrogen is not foreseeable. It therefore would be advantageous to provide specific methods and reagents useful for detecting, diagnosing, staging, monitoring, prognosticating, in vivo imaging, preventing, treating, or determining predisposition to diseases of the uterus. Such methods would include assaying a test sample for products of a gene(s) which are overexpressed in diseases and conditions associated with the uterus, including cancer. Such methods may further include assaying a test sample for products of a gene(s) whose distribution among the various tissues and compartments of the body have been altered by a uterus-associated disease or condition, including cancer. Such methods would comprise making cDNA from mRNA in the test sample, amplifying, when necessary, portions of the cDNA corresponding to the gene or a fragment thereof, and detecting the cDNA product as an indication of the presence of the disease or condition including cancer or detecting translation products of the mRNAs comprising gene sequences as an indication of the presence of the disease. Useful reagents include polynucleotides(s), or fragment(s) thereof which may be used in diagnostic methods such as reverse transcriptase-polymerase chain reaction (RT-PCR), PCR, or hybridization assays of mRNA extracted from biopsied tissue, blood, or other test samples; or proteins which are the translation products of such mRNAs; or antibodies directed against these proteins. Such assays would include methods for assaying a sample for product(s) of the gene and detecting the product(s) as an indication of disease of the breast. For example, these assays would include methods for detecting the gene products (proteins) in light of possible post-translational modifications that can occur in the body. Such post-translational modifications can include proteolytic processing, alteration of the chain termini, glycosylation, lipid attachment, sulfation, gamma-carboxylation, hydroxylation, phosphorylation, ADP-ribosylation, disulfide bond formation, and multiple non-covalent interactions with molecules such as co-factors, inhibitors (both small molecule and protein), activators (both small molecule and protein), and other proteins in formation of multi-subunit complexes. See, for example, T. E. Creighton et al., In: Proteins: Structures and Molecular Properties, Second Edition, pp. 78–102, New York, N.Y.: W. H. Freeman and Co. 1993.

Drug treatment or gene therapy for diseases and conditions of the uterus including cancer can be based on these identified gene sequences or their expressed proteins, and efficacy of any particular therapy can be monitored. Furthermore, it would be advantageous to have available alternative, less-invasive diagnostic methods capable of detecting early stage uterine disease, such as cancer.

All U.S. patents and publications referred to herein are hereby incorporated in their entirety by reference.

SUMMARY OF THE INVENTION

The subject invention relates to a purified multimeric polypeptide antigen (MPA) comprising at least one EU250 polypeptide (SEQ ID NO:3) and at least one polypeptide selected from the group consisting of a BU101 polypeptide (SEQ ID NO:2) and a TU104 polypeptide (SEQ ID NO:10). The antigen has a molecular weight of about 20–70 kilodaltons, an isoelectric point of about less than 8, and may further comprise at least one unknown polypeptide. This at least one unknown polypeptide has at least 20% identity with an amino acid sequence selected from the group consisting of SEQ ID NO:3, SEQ ID NO:2, SEQ ID NO:10, and fragments thereof. Furthermore, the at least one EU250 polypeptide and said at least one polypeptide selected from the group consisting of a BU101 polypeptide and a TU104 polypeptide are covalently linked by disulfide bonds. Additionally, the at least one BU101 polypeptide contains a polymorphism at amino acid position number 53 selected from the group consisting of proline and leucine.

The present invention also encompassses an antibody which specifically binds to at least one epitope of the antigen, wherein the epitope is derived from an amino acid sequence having at least 20% identity to an amino acid sequence selected from the group consisting of SEQ ID NO:3, SEQ ID NO:2, SEQ ID NO:10, and fragments thereof. The antibody may be monoclonal or polyclonal.

Moreover, the present invention also includes a method of detecting the presence of a multimeric polypeptide antigen (MPA) in a test sample suspected of containing the MPA, wherein the MPA comprises at least one EU250 polypeptide and at least one polypeptide selected from the group consisting of a BU101 polypeptide and a TU104 polypeptide, the method comprising the steps of: (a) contacting the test sample with at least one antibody specific for at least one epitope of the MPA for a time and under conditions sufficient to allow the formation of antigen/antibody complexes; and (b) detecting the complexes, wherein presence of the complexes indicates presence of the MPA in the test sample. Again, the MPA may further comprise at least one polypeptide selected from the group consisting of a TU104 polypeptide and a polypeptide having at least 20% identity with an amino acid sequence elected from the group consisting of SEQ ID NO:3, SEQ ID NO:2, SEQ ID NO:10, and fragments thereof. The at least one antibody is generated against a MPA, wherein said MPA is produced by a host cell transfected with a vector comprising a construct comprising at least one nucleotide sequence encoding at least one EU250 polypeptide and at least one nucleotide sequence encoding at least one polypeptide selected from the group consisting of a BU101 polypeptide and a TU104 polypeptide. Alternatively, the at least one antibody may be generated against a MPA, wherein the MPA is produced by a host cell comprising two vectors wherein one of the vectors comprises a construct comprising at least one nucleotide sequence encoding at least one EU250 polypeptide and wherein the other of the two vectors comprises a construct comprising at least one nucleotide sequence encoding at least one polypeptide selected from the group consisting of a BU101 polypeptide and a TU104 polypeptide.

Additionally, the present invention encompasses a method of detecting the presence of antibody specific for a multimeric polypeptide antigen (MPA), in a test sample suspected of containing the antibody, wherein the MPA comprises at least one EU250 polypeptide and at least one polypeptide selected from the group consisting of a BU101 polypeptide and a TU104 polypeptide, the method comprising the steps of: (a) contacting the test sample with a MPA comprising at least one epitope derived from an amino acid sequence or fragment thereof having at least 20% identity to an amino acid sequence selected from the group consisting of SEQ ID NO:3, SEQ ID NO:2, SEQ ID NO:10, and fragments thereof, for a time and under conditions sufficient to allow the formation of antibody/multimeric polypeptide antigen complexes; and (b) detecting the complexes, wherein presence of the complexes indicates presence of the antibody in the test sample. Again, the MPA may further comprise at least one polypeptide having at least 20% identity with an amino acid sequence selected from the group consisting of SEQ ID NO:3, SEQ ID NO:2, SEQ ID NO:10, and fragments thereof. The MPA may be produced by a host cell transfected with a vector comprising a construct comprising at least one nucleotide sequence encoding at least one EU250 polypeptide and at least one nucleotide sequence encoding at least one polypeptide selected from the group consisting of a BU101 polypeptide and a TU104 polypeptide. Alternatively, the MPA may be produced by a host cell comprising two vectors wherein one of the vectors comprises a construct comprising at least one nucleotide sequence encoding at least one EU250 polypeptide and wherein the other of the two vectors comprises a construct comprising at least one nucleotide sequence encoding at least one polypeptide selected from the group consisting of a BU101 polypeptide and a TU104 polypeptide. Additionally, it should be noted that the MPA may be attached to a solid phase.

The present invention also includes a method of detecting the presence of a multimeric polypeptide antigen (MPA) in a test sample suspected of containing the MPA, wherein the MPA comprises at least one EU250 polypeptide and at least one polypeptide selected from the group consisting of a BU101 polypeptide and a TU104 polypeptide, the method comprising the steps of: (a) contacting the test sample with at least one antibody specific for at least one epitope of the MPA for a time and under conditions sufficient to allow the formation of MPA/antibody complexes; (b) adding a conjugate to the resulting MPA/antibody complexes for a time and under conditions sufficient to allow the conjugate to bind to the bound antigen, wherein the conjugate comprises an antibody attached to a signal generating compound capable of generating a detectable signal; and (c) detecting the presence of the MPA which may be present in the test sample by detecting the signal generated by the signal generating compound. Once again, the MPA may further comprise at least one polypeptide having at least 20% identity with an amino acid sequence selected from the group consisting of SEQ ID NO:3, SEQ ID NO:2, SEQ ID NO:10, and fragments thereof. The antibody of step (a) may be generated against a MPA produced as described above. The at least one epitope of step (a) may be derived from a MPA, produced as described above.

Furthermore, the present invention also includes a method of detecting the presence of a multimeric polypeptide antigen (MPA) in a test sample suspected of containing the MPA, wherein the MPA comprises at least one EU250 polypeptide and at least one polypeptide selected from the group consisting of a BU101 polypeptide and a TU104 polypeptide, the method comprising the steps of: (a) contacting the test sample with at least one antibody specific for at least one epitope of the MPA for a time and under conditions sufficient to allow the formation of MPA/antibody complexes; (b) adding a conjugate to the resulting MPA/antibody complexes for a time and under conditions sufficient to allow the conjugate to bind to the bound antigen, wherein the conjugate comprises a steroid or antibody, attached to a signal generating compound capable of generating a detectable signal; and (c) detecting the presence of the MPA which may be present in said test sample by detecting the signal generated by the signal generating compound. The MPA may further comprise at least one polypeptide having at least 20% identity with an amino acid sequence selected from the group consisting of SEQ ID NO:3, SEQ ID NO:2, SEQ ID NO:10, and fragments thereof. The steroid may be selected from the group consisting of progesterone, aldosterone, androstenedione, corticosterone, cortisol, dehydroepiandrosterone, dihydrotestosterone, estradiol, estriol, estrone, hydroxyprogesterone, and testosterone. The antibody of step (a) may be generated against a MPA, produced as described above.

The present invention also includes a method of detecting the presence of antibody specific for a multimeric polypeptide antigen (MPA) in a test sample suspected of containing the antibody, wherein the MPA comprises at least one EU250 polypeptide and at least one polypeptide selected from the group consisting of a BU101 polypeptide and a TU104 polypeptide, the method comprising the steps of: (a) contacting the test sample with at least one MPA epitope derived from an amino acid sequence or fragment thereof having at least 20% identity to an amino acid sequence selected from the group consisting of SEQ ID NO:3, SEQ ID NO:2, SEQ ID NO:10, and fragments thereof, for a time and under conditions sufficient to allow the formation of MPA/antibody complexes; (b) adding a conjugate to the resulting MPA/antibody complexes for a time and under conditions sufficient to allow the conjugate to bind to the bound antibody, wherein the conjugate comprises 1) an antibody, which binds with the antibody in the test sample, attached to 2) a signal generating compound capable of generating a detectable signal; and (c) detecting the presence of said antibody which may be, present in the test sample by detecting the signal generated by the signal generating compound. Again, the multimeric polypeptide antigen may further comprise at least one polypeptide having at least 20% identity with an amino acid sequence elected from the group consisting of SEQ ID NO:3, SEQ ID NO:2, SEQ ID NO:10, and fragments thereof. The at least one MPA epitope of step (a) is derived from a MPA, wherein the MPA is produced by a host cell transfected with a vector comprising a construct comprising at least one nucleotide sequence encoding at least one EU250 polypeptide and at least one nucleotide sequence encoding at least one polypeptide selected from the group consisting of a BU101 polypeptide and a TU104 polypeptide. Alternatively, as noted above, the at least one epitope of step (a) may be derived from a MPA, wherein the MPA is produced by a host cell comprising two vectors wherein one of the vectors comprises a construct comprising at least one nucleotide sequence encoding at least one EU250 polypeptide and wherein the other of the two vectors comprises a construct comprising at least one nucleotide sequence encoding at least one polypeptide selected from the group consisting of a BU101 polypeptide and a TU104 polypeptide.

Also, the present invention includes an assay kit for determining the presence of antibody specific for a multimeric polypeptide antigen (MPA) in a test sample suspected of containing the antibody, the assay kit comprising a container containing a MPA, wherein the MPA comprises an epitope having at least 20% identity with an amino acid sequence selected from the group consisting of SEQ ID NO:3, SEQ ID NO:2, SEQ ID NO:10, and fragments thereof. The antigen in the container may be attached to a solid phase. The assay kit may further comprise at least one member selected from the group consisting of a reducing agent and a detergent.

Moreover, the present invention also encompasses an assay kit for determining the presence of a multimeric polypeptide antigen (MPA), in a test sample suspected of containing the antigen, comprising a container containing an antibody which specifically binds to a MPA comprising at least one epitope having an amino acid sequence having at least 20% identity with an amino acid sequence selected from the group consisting of SEQ ID NO:3, SEQ ID NO:2, SEQ ID NO:10, and fragments thereof. The assay kit may further comprises at least one member selected from the group consisting of a reducing agent and a detergent. The antibody may be generated against a MPA, wherein said MPA is produced by a method as described above.

The present invention also includes a method for producing antibodies which specifically bind to a multimeric polypeptide antigen (MPA), comprising administering to an individual an isolated immunogenic polypeptide or fragment thereof in an amount sufficient to elicit an immune response, wherein the immunogenic polypeptide or fragment thereof comprises at least one MPA epitope having at least 20% identity to an amino acid sequence selected from the group consisting of SEQ ID NO:3, SEQ ID NO:2, SEQ ID NO:10, and fragments thereof.

The present invention also includes a composition of matter comprising a multimeric polypeptide antigen, wherein the antigen comprises at least one EU250 polypeptide and at least one polypeptide selected from the group consisting of a BU101 polypeptide and a TU104 polypeptide. The antigen may further comprise at least one polypeptide having at least 20% identity with an amino acid sequence selected from the group consisting of SEQ ID NO:3, SEQ ID NO:2, SEQ ID NO:10, and fragments thereof. The composition may further comprise at least one antibody, bound to the multimeric polypeptide antigen, wherein the antibody is specific to at least one polypeptide selected from the group consisting of a EU250 polypeptide, a BU101 polypeptide, a TU104 polypeptide, a polypeptide having at least 20% identity with an amino acid sequence selected from the group consisting of SEQ ID NO:3, SEQ ID NO:2, SEQ ID NO:10, and fragments thereof. For example, the composition may comprise two antibodies wherein each binds to a separate polypeptide having an amino acid sequence having at least 20% identity with an amino acid sequence selected from the group consisting of SEQ ID NO:3, SEQ ID NO:2, SEQ ID NO:10, and fragments thereof. In particular, each of the two antibodies may bind to a EU250 polypeptide or a fragment thereof or a polypeptide selected from the group consisting of a BU101 polypeptide, a TU104 polypeptide, and fragments thereof. Alternatively, one of the two antibodies may bind to a EU250 polypeptide or a fragment thereof and the other of the two antibodies may bind to a polypeptide selected from the group consisting of a BU101 polypeptide, a TU104 polypeptide, and fragments thereof. Also, one of the two antibodies may bind to a EU250 polypeptide or fragment thereof and the other of the two antibodies may bind to a polypeptide having an amino acid sequence having at least 20% identity with an amino acid sequence selected from the group consisting of SEQ ID NO:3, SEQ ID NO:2, SEQ ID NO:10, and fragments thereof. Or, one of the two antibodies may bind to a polypeptide selected from the group consisting of a BU101 polypeptide, a TU104 polypeptide, and fragments thereof, and the other of the two antibodies may bind to a polypeptide having an amino acid sequence having at least 20% identity with an amino acid sequence selected from the group consisting of SEQ ID NO:3, SEQ ID NO:2, SEQ ID NO:10, and fragments thereof.

Additionally, the present invention also encompasses a method of detecting uterine cancer in a patient suspected of having uterine cancer comprising the steps of: (a) administering to the patient a labelled antibody specific to a multimeric protein antigen (MPA), wherein the MPA comprises at least one EU250 polypeptide and at least one polypeptide selected from the group consisting of a BU101 polypeptide and a TU104 polypeptide; and (b) localizing presence of the label, presence of the label indicating presence of MPA and uterine cancer in the patient. Again, the MPA may further comprise at least one polypeptide having at least 20% identity with an amino acid sequence selected from the group consisting of SEQ ID NO:3, SEQ ID NO:2, SEQ ID NO:10, and fragments thereof. The antibody of step (a) is generated against a MPA, wherein the MPA is produced by any of the methods described above (i.e., using one vector or two).

The present invention also includes a method of treating breast cancer in a patient comprising administering to the patient an antibody specific to a multimeric polypeptide antigen (MPA), the MPA comprising at least one EU250 polypeptide and at least one polypeptide selected from the group consisting of a BU101 polypeptide and a TU104 polypeptide. The MPA may further comprise at least one polypeptide having at least 20% identity with an amino acid sequence selected from the group consisting of SEQ ID NO:3, SEQ ID NO:2, SEQ ID NO:10, and fragments thereof. The antibody may be generated against a MPA, wherein said MPA is produced is produced by one of the methods described above.

Additionally, the present invention includes a method of diagnosing uterine cancer in a patient suspecting of having uterine cancer comprising the steps of: (a) preparing a tissue section or cell culture derived from a tumor excised from the patient; (b) exposing the tissue section or cell culture to an antibody specific for at least one polypeptide of a multimeric polypeptide antigen (MPA) for a time and under conditions sufficient to allow formation of antigen/antibody complexes, the polypeptide selected from the group consisting of a EU250 polypeptide, a BU101 polypeptide, a TU104 polypeptide, a polypeptide having at least 20% identity with an amino acid sequence selected from the group consisting of SEQ ID NO:3, SEQ ID NO:4, SEQ ID NO:0, and fragments thereof; and (c) localizing presence of the complexes in the tissue section or cell culture, presence of the complexes indicating presence of MPA and uterine cancer in the patient. The antibody is generated against a MPA, wherein the MPA is produced in accordance with one of the methods described above.

Furthermore, the present invention includes a method of diagnosing uterine cancer in a patient suspected of having uterine cancer comprising the steps of detecting the presence or absence of at least one polypeptide of a multimeric polypeptide antigen (MPA), said polypeptide selected from the group consisting of a EU250 polypeptide, a BU101 polypeptide, a TU104 polypeptide and a polypeptide having at least 20% identity with an amino acid sequence selected from the group consisting of SEQ ID NO:3, SEQ ID NO:2, SEQ ID NO:10, and fragments thereof, in a biological sample from the patient, presence of the at least one polypeptide indicating presence of MPA and uterine cancer in the patient. The biological sample may be selected from the group consisting of tissue, urine, bone marrow and blood.

The present invention also encompasses a method of diagnosing uterine cancer in a patient suspected of having uterine cancer comprising the steps of detecting the presence or absence of extracellular BU101 in said patient, presence of extracellular BU101 indicating breast cancer in the patient and transport of BU101 outside cells via EU250 in a multimeric polypeptide antigen (MPA), the MPA comprising at least one EU250 polypeptide and at least one BU101 polypeptide. The MPA, again, may further comprise at least one polypeptide selected from the group consisting of a TU104 polypeptide and a polypeptide having at least 20% identity with an amino acid sequence selected from the group consisting of SEQ ID NO:3, SEQ ID NO:2, SEQ ID NO:10, and fragments thereof.

Additionally, the present invention includes a method of detecting uterine cancer in a patient suspected of having uterine cancer comprising the steps of: (a) obtaining a biological sample from the patient; (b) measuring the amount of free EU250 polypeptide in the biological sample; (c) measuring the amount of EU250 polypeptide, present in said biological sample, complexed to at least one polypeptide selected from the group consisting of a BU101 polypeptide and a TU104 polypeptide; and (d) comparing the ratio of free EU250 polypeptide to complexed EU250 polypeptide, a ratio higher than 1 indicating presence of uterine cancer in the patient.

The present invention also includes a method of detecting uterine cancer in a patient suspecting of having uterine cancer comprising the steps of: (a) obtaining a biological sample from the patient; (b) measuring the amount of a free polypeptide selected from the group consisting of a BU101 polypeptide and a TU104 polypeptide in the biological sample; (c) measuring the amount of a polypeptide selected from the group consisting of a BU101 polypeptide and a TU104 polypeptide, present in the biological sample, wherein the polypeptide is the same as the free polypeptide of step (b), complexed to EU250 polypeptide; and (d) comparing the ratio of the free polypeptide to complexed polypeptide, a ratio higher than 1 indicating presence of uterine cancer in the patient.

Furthermore, the present invention also encompasses a method for enhancing recognition of MPA, in an immunoassay for MPA, comprising exposing the MPA to at least one member selected from the group consisting of a reducing agent and a detergent, prior to contacting said MPA with an antibody or chemical compound. The method may further comprise the step of exposing the MPA to heat.

The present invention also includes a method for dissociating MPA comprising exposing the MPA to at least one member selected from the group consisting of a reducing agent and a detergent. This method may also further comprise the step of exposing the MPA to heat.

Additionally the present invention includes diagnostic reagent produced by a host cell transfected with a vector comprising a construct comprising at least one nucleotide sequence which encodes at least one EU250 polypeptide and at least one nucleotide sequence which encodes at least one polypeptide selected from the group consisting of a BU101 polypeptide and a TU104 polypeptide.

The present invention also includes a diagnostic reagent produced by a host cell transfected with two vectors wherein one of the two vectors comprises a construct comprising at least one nucleotide sequence which encodes at least one EU250 polypeptide and wherein the other of the two vectors comprises a construct comprising at least one nucleotide sequence which encodes at least one polypeptide selected from the group consisting of a BU101 polypeptide and a TU104 polypeptide.

Additionally, the present invention includes a method for detecting the presence of a multimeric polypeptide antigen (MPA) in a test sample suspected of containing the MPA, wherein the MPA comprises at least one EU250 polypeptide and at least one polypeptide selected from the group consisting of a BU101 polypeptide and a TU104 polypeptide, said method comprising the steps of: (a) contacting the test sample with a labelled antigen selected from the group consisting of a MPA, a polypeptide of MPA, a fragment of MPA and a fragment of a polypeptide of MPA; (b) contacting the test sample and labelled antigen of step (a) with an anti-MPA antibody for a time and under conditions sufficient to allow for the formation of MPA/anti-MPA complexes; and (c) detecting the presence of MPA which may be present in the test sample by detecting a signal generated by the labelled antigen.

Furthermore, the present invention also includes a method for detecting the presence of a multimeric polypeptide antigen (MPA) in a test sample suspected of containing the MPA, wherein the MPA comprises at least one EU250 polypeptide and at least one polypeptide selected from the group consisting of a BU101 polypeptide and a TU104 polypeptide, said method comprising the steps of: (a) contacting the test sample with a labelled antibody which binds to MPA for a time and under conditions sufficient for the formation of MPA/labelled antibody complexes; (b) contacting the complexes of step (a) with an antigen selected from the group consisting of a MPA, a polypeptide of MPA, a fragment of a MPA and a fragment of a polypeptide of a MPA for a time and under conditions sufficient for the formation of antigen/labelled antibody complexes; and (c) detecting the presence of a signal generated by the labelled antibody, wherein the signal is indicative of the presence of MPA in the test sample.

Additionally, the present invention includes a method for detecting the presence of a multimeric polypeptide antigen (MPA) in a test sample suspected of containing the MPA, wherein the MPA comprises at least one EU250 polypeptide and at least one polypeptide selected from the group consisting of a BU101 polypeptide and a TU104 polypeptide, the method comprising the steps of: (a) contacting the test sample with a labelled steroid which binds to MPA for a time and under conditions sufficient for the formation of MPA/labelled steroid complexes; (b) contacting the MPA/labelled steroid complexes of step (a) with an antigen selected from the group consisting of a MPA, a polypeptide of a MPA, a fragment of a MPA, and a fragment of a polypeptide of a MPA, for a time and under conditions sufficient to allow for the formation of antigen/labelled steroid complexes; and (c) detecting the presence of MPA which may be present in the test sample by detecting a signal generated by the labelled steroid.

Also, the present invention includes a method for detecting the presence of a multimeric polypeptide antigen (MPA)

in a test sample suspected of containing the MPA, wherein the MPA comprises at least one EU250 polypeptide and at least one polypeptide selected from the group consisting of a BU101 polypeptide and a TU104 polypeptide, said method comprising the steps of: (a) contacting the test sample with a steroid for a time and under conditions sufficient to allow for the formation of MPA/steroid complexes; (b) adding a conjugate to the resulting MPA/steroid complexes for a time and under conditions sufficient to allow said conjugate to bind to the bound MPA, wherein the conjugate comprises an antibody attached to a signal generating compound capable of generating a detectable signal; and (c) detecting the presence of the MPA which may be present in the test sample by detecting the signal generated by said signal generating compound. In all of the above methods involving the detecting of a MPA, the test sample may be exposed to at least one member selected from the group consisting of a reducing agent and a detergent, prior to contacting the sample with an antibody or a chemical compound.

The present invention also includes a method for detecting the presence of antibody specific for a multimeric polypeptide antigen (MPA) in a test sample suspected of containing the antibody, the method comprising the steps of: (a) contacting the test sample with an anti-antibody for a time and under conditions sufficient to allow for the formation of antibody/anti-antibody complexes; (b) adding a conjugate to the resulting antibody/anti-antibody for a time and under conditions sufficient to allow said conjugate to bind to the bound antibody, wherein the conjugate comprises MPA attached to a signal generating compound capable of generating a detectable signal; and (c) detecting the presence of the antibody which may be present in the test sample by detecting the signal generated by the signal generating compound.

Additionally, the present invention encompasses a method for detecting the presence of an antibody specific for a MPA in a test sample suspected of containing the antibody, the method comprising the steps of: (a) contacting the test sample with a labelled antigen selected from the group consisting of a MPA, a polypeptide of a MPA, a fragment of a MPA, and a fragment of a polypeptide of a MPA, for a time and under conditions sufficient to allow for the formation of antibody/labelled antigen complexes; (b) contacting the resulting complexes of step (a) with an antibody which binds to MPA, for a time and under conditions sufficient to allow unbound, labelled antigen to bind to the antibody which binds to MPA; and (c) detecting the presence of the antibody which may be present in the test sample by detecting the signal generated by the labelled antigen.

The present invention also includes a method of detecting the presence of an antibody specific for a multimeric polypeptide antigen (MPA) in a test sample suspected of containing the antibody, wherein the MPA comprises at least one EU250 polypeptide and at least one polypeptide selected from the group consisting of a BU101 polypeptide and a TU104 polypeptide, the method comprising the steps of: (a) contacting the test sample with a MPA complexed with a steroid, for a time and under conditions sufficient to allow for formation of antibody/MPA/steroid complexes; (b) adding a conjugate to the resulting antibody/MPA/steroid complexes for a time and under conditions sufficient to allow the conjugate to bind to bound antibody, wherein the conjugate comprises an antibody, reactive with the antibody in the test sample, attached to a signal generating compound capable of generating a detectable signal; and (c) detecting the presence of the antibody which may be present in the test sample by detecting the signal generated by the signal generating compound.

BRIEF DESCRIPTION OF THE DRAWINGS

FIG. 1 is an alignment of the members of the Uteroglobin family of proteins.

DETAILED DESCRIPTION OF THE INVENTION

Figure 2:
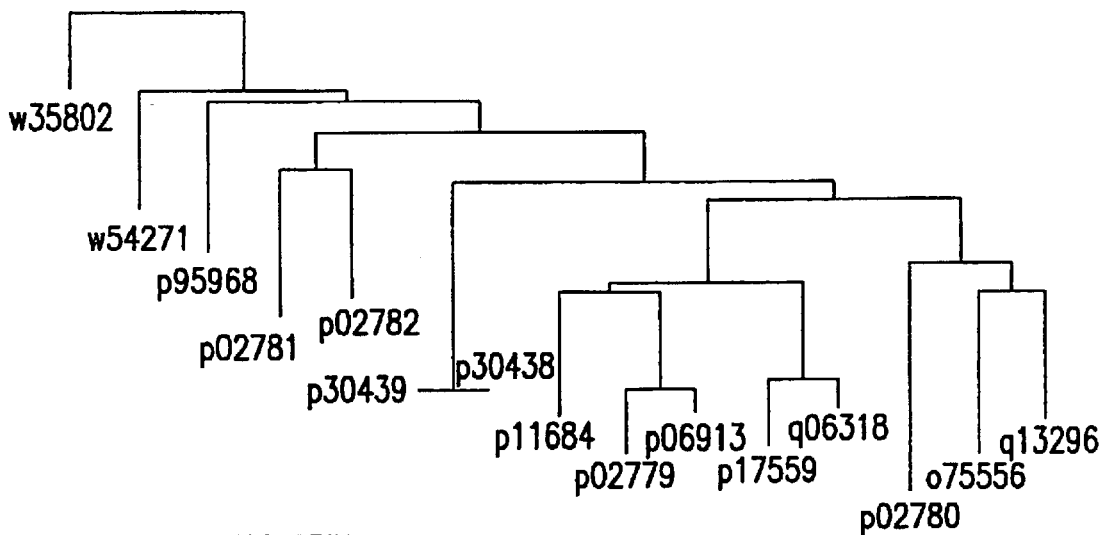
FIG. 2 is a phylogram produced from the sequence alignment of FIG. 1 using the algorithms, Distances and Growtree (Genetics Computer Group, Madison, Wis.).

The present invention provides a new entity, specifically, a multimeric polypeptide complex, wherein at least one copy of a EU250 polypeptide (SEQUENCE ID NO:3) and at least one copy of either a BU101 polypeptide (SEQUENCE ID NO:2) or a TU104 polypeptide (SEQUENCE ID NO:10), or both, are present. Additionally, the complex may further comprise one or more unknown polypeptides.

EU250 may be linked covalently, via disulfide bonds, to either BU101 or TU104. In the case where the complex comprises EU250 and BU101, both polypeptides contain 3 cysteine residues in their mature form. This disulfide linked heterodimer may constitute one subunit of the complex and it may have interactions with another subunit of identical composition, forming an $\alpha\beta/\alpha\beta$ heterotetramer; or, it may interact with a subunit of nonidentical composition, forming an $\alpha\beta/\alpha'\beta$, or an $\alpha\beta/\alpha\beta'$, or an $\alpha\beta/\alpha'\beta'$ heterotetramer, where $\alpha$ represents BU101, $\beta$ represents EU250, $\alpha'$ represents a sequence homologous to but not identical to BU101, for example, TU104, and $\beta'$ represents a sequence homologous to but not identical to EU250, for example, Mammaglobin BU101 polypeptide sequence and TU104 polypeptide sequence are homologous sequences with an identity score of 59% (53 residues identical over 90 amino acids), and a similarity score of 62%. However, each sequence could have homologous sequences to itself which would not be homologous to the other. As the identity between two sequences (1 and 2) diminishes, so does the chance that a third sequence, homologous to one (1), will have equal homology to the other (2), and vice versa. Therefore, for purposes of the present invention, a complex comprising BU101, EU250 and TU104 is designated as $\alpha\beta\gamma$ wherein "$\alpha$" is BU101, "$\beta$" is EU250, and "$\gamma$" is TU104.

In the case where the complex comprises EU250 and TU104, both polypeptides contain 3 cysteine residues in their mature form. This disulfide linked heterodimer may constitute one subunit of the complex and it may have interactions with another subunit of identical composition, forming a $\gamma\beta/\gamma\beta$ heterotetramer; or, it may interact with a subunit of nonidentical composition, forming a $\gamma\beta/\gamma'\beta$, or a $\gamma\beta/\gamma\beta'$, or an $\gamma\beta/\gamma'\beta'$ heterotetramer, where $\gamma$ represents TU104, $\beta$ represents EU250, $\gamma'$ represents a sequence homologous to but not identical to TU104, for example, BU101, and $\beta'$ represents a sequence homologous to but not identical to EU250, for example, Mammaglobin.

The BU101 gene may contain a T/C polymorphism at position 254 of the BU101 polynucleotide sequence (SEQUENCE ID NO:1). This polymorphism results in either the amino acid proline (CCG) or the amino acid leucine (CTG) at this position. No biological difference was observed in any experiments described in this invention between the two BU101 nucleotide variants, or in the respectively expressed polypeptides. The multimeric polypeptide complex can be produced by recombinant technology, produced by isolation from natural sources, or produced by synthetic techniques.

The present invention provides another new entity, specifically, a multimeric polypeptide complex, wherein at least one copy of a LU103 polypeptide (SEQUENCE ID NO:7) and at least one copy of a LU105 polypeptide (SEQUENCE ID NO:9) are present. Additionally, the complex may further comprise one or more unknown polypeptides.

LU103 may be linked covalently, via disulfide bonds, to LU105. In the case where the complex comprises LU103 and LU105, both polypeptides contain 1 cysteine residue in their mature form. This disulfide linked heterodimer may constitute one subunit of the complex and it may have interactions with another subunit of identical composition, forming a δε/δεheterotetramer; or, it may interact with a subunit of nonidentical composition, forming a δε/δ'ε, or a δε/δε', or a δε/δ'ε' heterotetramer, where δ represents LU103, ε represents LU105, δ' represents a sequence homologous to but not identical to LU103, and ε' represents a sequence homologous to but not identical to LU105.

The present invention also provides methods for assaying a test sample for this multimeric polypeptide complex which comprises making reagents such as polypeptides, including but not limited to, whole or partial sequences of the component polypeptide chains of the multimeric polypeptide complex, and antibodies against these antigens. Test samples which may be assayed by the methods provided herein include tissues, cells, body fluids including urine, and secretions.

Portions of the polypeptide sequences are useful as standards or reagents in diagnostic immunoassays, as targets for pharmaceutical screening assays and/or as components or as target sites for various therapies. Monoclonal and polyclonal antibodies directed against at least one epitope contained within these polypeptide sequences are useful as delivery agents for therapeutic agents as well as for diagnostic tests and for screening for diseases or conditions associated with the multimeric polypeptide complex, especially breast cancer.

Techniques for determining amino acid sequence "similarity" are well-known in the art. In general, "similarity" means the exact amino acid to amino acid comparison of two or more polypeptides at the appropriate place, where amino acids are identical or possess similar chemical and/or physical properties such as charge or hydrophobicity. A so-termed "percent similarity" then can be determined between the compared polypeptide sequences. Techniques for determining amino acid sequence identity also are well known in the art and include determining the amino acid sequence and comparing this to a second amino acid sequence. In general, "identity" refers to an exact amino acid to amino acid correspondence of two polypeptide sequences. Two or more amino acid sequences can be compared by determining their "percent identity." The percent identity of two sequences, peptide sequences, is the number of exact matches between two aligned sequences divided by the length of the shorter sequences and multiplied by 100. An approximate alignment for sequences is provided by the local homology algorithm of Smith and Waterman, Advances in Applied Mathematics 2: 482–489 (1981). This algorithm can be extended to use with peptide sequences using the scoring matrix developed by Dayhoff, Atlas of Protein Sequences and Structure, M. O. Dayhoff ed., 5 suppl. 3: 353–358, National Biomedical Research Foundation, Washington, D.C., USA, and normalized by Gribskov, Nucl. Acids Res. 14(6): 6745–6763 (1986). An implementation of this algorithm for peptide sequences is provided by the Genetics Computer Group (Madison, Wis.) in their BestFit utility application. The default parameters for this method are described in the Wisconsin Sequence Analysis Package Program Manual, Version 8 (1995) (available from Genetics Computer Group, Madison, Wis.). Other equally suitable programs for calculating the percent identity or similarity between sequences are generally known in the art.

The compositions and methods described herein will enable the identification of certain markers as indicative of a reproductive tissue disease or condition, for example uterine cancer; the information obtained therefrom will aid in the detecting, diagnosing, staging, monitoring, prognosticating, in vivo imaging, preventing or treating, or determining diseases or conditions associated with the multimeric polypeptide complex, especially uterine cancer. Test methods include, for example, immunoassays which utilize the multimeric polypeptide complex provided herein.

This multimeric polypeptide complex contains unique epitopes which may be found to be immunogenic. These epitopes are believed to be unique to the disease state or condition associated with the multimeric polypeptide complex. It is also thought that the multimeric polypeptide complex is useful as a marker. This marker is either elevated in disease such as uterine cancer, altered in disease such as uterine cancer, or present as a normal protein complex but appearing in an inappropriate body compartment. The uniqueness of the epitope(s) may be determined by (i) their immunological reactivity and specificity with antibodies directed against proteins and polypeptides encoded by the BU101 gene (SEQUENCE ID NO:1), the EU250 gene (SEQUENCE ID NO:4), the TU104 gene (SEQUENCE ID NO:5), the α', β' or γ' genes, when present in the complex; and (ii) the absence of cross-reactivity with any other tissue markers. Methods for determining immunological reactivity are well-known and include, but are not limited to, for example, radioimmunoassay (RIA), enzyme-linked immunoabsorbent assay (ELISA), hemagglutination (HA), fluorescence polarization immunoassay (FPIA), chemiluminescent immunoassay (CLIA) and others. Several examples of suitable methods are described herein.

Furthermore, the biological synthesis and assembly of the multimeric polypeptide complex within a cell is highly regulated under normal conditions. Under conditions of disease, the synthesis and assembly of the multimeric polypeptide complex may become deregulated. Deregulation of transcriptional activation may cause an up-regulation or down-regulation of that gene product. Under circumstances where the gene of only one of the component polypeptide chains is up-regulated, increased levels of this gene product may be transcribed and translated into polypeptide. This may cause an accumulation of the single polypeptide independent of other components of the multimeric polypeptide complex. The measurement of the multimeric polypeptide complex with respect to the free or total amounts of the component polypeptides of the multimeric polypeptide complex is an indication of this deregulation and may indicate a disease such as uterine cancer.

Furthermore, deregulation of the synthesis and assembly of the multimeric polypeptide complex may result in overproduction/accumulation of any one of the component polypeptide chains of this complex. Under normal circumstances, the multimeric polypeptide complex is found secreted from the mammalian cell of origin. However, individual component polypeptide chains, independent of other components of the multimeric polypeptide complex, may not undergo the same processing. For example, the expression of BU101 polypeptide, independent of other polypeptides of the multimeric polypeptide complex, may result in a non-secreted form of the polypeptide that is retained inside the cell. The accumulation of free BU101 or other component polypeptide chains inside the cell may result from aberrations in transcription and/or translation, and may be a result of disease such as cancer.

Furthermore, cellular damage and disruption may result in the release of BU101 polypeptide (SEQUENCE ID NO:2) from inside the cell without its multimeric, paired polypeptide chair. This may lead to accumulation of BU101 polypeptide or other component polypeptide chains in the interstitial fluid surrounding the cells. Furthermore, tissue damage and disruption may result in the release of BU101 polypeptide (SEQUENCE ID NO:2) or other component polypeptide chains from the tissue without its respective, paired polypeptide chain. Both cellular and tissue damage/disruption may be a result of disease such as uterine cancer.

Unless otherwise stated, the following terms shall have the following meanings:

"Encoded by" refers to a nucleic acid sequence which codes for a polypeptide sequence, wherein the polypeptide sequence or a portion thereof contains an amino acid sequence of at least 3 to 5 amino acids, more preferably at least 8 to 10 amino acids, and even more preferably at least 15 to 20 amino acids from a polypeptide encoded by the nucleic acid sequence. Also encompassed are polypeptide sequences which are immunologically identifiable with a polypeptide encoded by the sequence. Thus, a "polypeptide," "protein," or "amino acid" sequence has at least about 50% identity, preferably about 60% identity, more preferably about 75–85% identity, and most preferably about 90–95% or more identity with an amino acid sequence encoded by a EU250 gene (SEQUENCE ID NO:4), a BU101 gene (SEQUENCE ID NO:1), a TU104 gene (SEQUENCE ID NO:5), or an α', β' or γ' gene (i.e., the genes whose encoded polypeptides form the multimeric polypeptide complex). Further, the "polypeptide," "protein," or "amino acid" sequence encoded by the EU250 gene (SEQUENCE ID NO:4), BU101 gene (SEQUENCE ID NO:1), TU104 gene (SEQUENCE ID NO:5), α' gene, β' gene, or γ' gene (i.e., the genes whose encoded polypeptides form the multimeric polypeptide complex) may have at least about 60% similarity, preferably at least about 75% similarity, more preferably about 85% similarity, and most preferably about 95% or more similarity to a polypeptide or amino acid sequence of the EU250 gene (SEQUENCE ID NO:4), BU101 gene (SEQUENCE ID NO:1), TU104 gene (SEQUENCE ID NO:5), α' gene, β' gene, or γ' gene.

A "recombinant polypeptide," "recombinant protein," or "a polypeptide produced by recombinant techniques," which terms may be used interchangeably herein, describes a polypeptide which by virtue of its origin or manipulation is not associated with all or a portion of the polypeptide with which it is associated in nature and/or is linked to a polypeptide other than that to which it is linked in nature. A recombinant or encoded polypeptide or protein is not necessarily translated from a designated nucleic acid sequence. It also may be generated in any manner, including chemical synthesis or expression of a recombinant expression system.

The term "synthetic peptide" as used herein means a polymeric form of amino acids of any length, which may be chemically synthesized by methods well-known to the routineer. These synthetic peptides are useful in various applications.

"Purified polypeptide" or "purified protein" means a polypeptide of interest or fragment thereof which is essentially free of, e.g., contains less than about 50%, preferably less than about 70%, and more preferably less than about 90%, cellular components with which the polypeptide of interest is naturally associated. Methods for purifying polypeptides of interest are known in the art.

The term "isolated" means that the material is removed from its original environment (e.g., the natural environment if it is naturally occurring). For example, a naturally-occurring polynucleotide or polypeptide present in a living animal is not isolated, but the same polynucleotide or DNA or polypeptide, which is separated from some or all of the coexisting materials in the natural system, is isolated. Such polynucleotide could be part of a vector and/or such polynucleotide or polypeptide could be part of a composition, and still be isolated in that the vector or composition is not part of its natural environment.

"Polypeptide" and "protein" are used interchangeably herein and include all polypeptides as described below. The basic structure of polypeptides is well known and has been described in innumerable textbooks and other publications in the art. In this context, the term is used herein to refer to any peptide or protein comprising two or more amino acids joined to each other in a linear chain by peptide bonds. As used herein, the term refers to both short chains, which also commonly are referred to in the art as peptides, oligopeptides and oligomers, for example, and to longer chains, which generally are referred to in the art as proteins, of which there are many types.

It will be appreciated that polypeptides often contain amino acids other than the 20 amino acids commonly referred to as the 20 naturally occurring amino acids, and that many amino acids, including the terminal amino acids, may be modified in a given polypeptide, either by natural processes, such as processing and other post-translational modifications, but also by chemical modification techniques which are well known to the art. Even the common modifications that occur naturally in polypeptides are too numerous to list exhaustively here, but they are well described in basic texts and in more detailed monographs, as well as in a voluminous research literature, and they are well known to those of skill in the art. Among the known modifications which may be present in polypeptides of the present are, to name an illustrative few, acetylation, acylation, ADP-ribosylation, amidation, covalent attachment of flavin, covalent attachment of a heme moiety, covalent attachment of a nucleotide or nucleotide derivative, covalent attachment of a lipid of lipid derivative, covalent attachment of phosphatidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myrisoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as for instance Proteins—Structure and Molecular Properties, $2^{nd}$ Ed., T. E. Creighton, W. H. Freeman and Company, New York (1993). Many detailed reviews are available on this subject, such as, for example, those provided by Wold, F., Posttranslational Protein Modifications: Perspectives and Prospects, pg. 1–12 in Posttranslational Covalent Modification of Proteins, B. C. Johnson, Ed., Academic Press, New York (1983); Seifter et al., Analysis for protein modifications and nonprotein cofactors, Meth. Enzymol. 182: 626–646 (1990) and Rattan et al., Protein synthesis: Posttranslational Modifications and Aging, Ann N.Y. Acad. Sci. 663: 48–62(1992).

It will be appreciated, as is well known and as noted above, that polypeptides are not always entirely linear. For instance, polypeptides may be branched as a result of ubiquitination, and they may be circular, with or without branching, generally as a result of posttranslational events, including natural processing events and events brought about by human manipulation which do not occur naturally. Circular, branched, and branched circular polypeptides may be synthesized by non-translational natural process and by entirely synthetic methods as well.

Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides. For instance, the amino terminal residue of polypeptides made in $E.\ coli$, prior to proteolytic processing, almost invariably will be N-formylmethionine.

The modifications that occur in a polypeptide often will be a function of how it is made. For polypeptides made by expressing a cloned gene in a host, for instance, the nature and extent of the modifications in large part will be determined by the host cell posttranslational modification capacity and the modification signals present in the polypeptide amino acid sequence. For instance, as is well known, glycosylation often does not occur in bacterial hosts such as $E.\ coli$. Accordingly, when glycosylation is desired, a polypeptide should be expressed in a glycosylating host, generally a eukaryotic cell. Insect cells often carry out the same posttranslational glycosylations as mammalian cells, and, for this reason, insect cell expression systems have been developed to express efficiently mammalian proteins having native patterns of glycosylation. Similar considerations apply to other modifications.

It will be appreciated that the same type of modification may be present in the same or varying degree at several sites in a given polypeptide. Also, a given polypeptide may contain many types of modifications.

In general, as used herein, the term polypeptide encompasses all such modifications, particularly those that are present in polypeptides synthesized by expressing a polynucleotide in a host cell.

A "multimeric polypeptide complex" and "multimeric polypeptide antigen" and "polypeptide complex" are used interchangeably herein and refer to an entity comprising at least two or more separate individual polypeptide chains. These chains, either identical or different, can be covalently or non-covalently associated. These polypeptide chains can be produced recombinantly, synthesized chemically, or isolated from natural sources. Techniques, known to those in the art, are available for creating a multimeric polypeptide complex from individual chains.

The simplest example of such a multimeric polypeptide complex is a dimer, wherein the individual chains are identical. These chains may be covalently linked, for example, by disulfide bonds, or may be non-covalently associated, for example, by hydrogen bonds and electrostatic interactions. A slightly more complex example is a dimer, wherein the individual chains are non-identical. Again, these chains may be covalently or non-covalently linked. Another level of complexity in a multimeric polypeptide complex would be the increased number of individual chains contributing to the complex, forming trimers, tetramers, pentamers, and higher-order complexes. Again, some chains may interact covalently while others interact non-covalently. Such arrangements may be observed in a crystal structure or solution structure of the protein, and the detailed nature of the interactions that produce the structure become apparent. For example, hemoglobin has 4 individual chains in its complex, 2 of which are of one sequence ($\alpha$), and 2 of which are of another sequence ($\beta$), forming an $\alpha_2\beta_2$ heterotetramer. Another example is $E.\ coli$ RNA polymerase having the arrangement $\alpha_2\beta\beta'\sigma$, where 2 $\alpha$ chains, 1 $\beta$ chain, 1 $\beta'$ chain (homologous to but not identical to $\beta$, for example, Mammaglobin) and 1 $\sigma$ chain make up the complex. Many more complex cases are known. Some proteins have large numbers of each of several chains, still with a fixed total size and stoichiometry, for example, pyruvate dehydrogenase $[t_{24}(p_2)_{12}(f_2)_{12}]$ which is composed of 24 copies of subunit, t, 12 copies of the homodimer, $p_2$, and 12 copies of the homodimer, $f_2$. Others are polymeric structures where the relative composition may be fixed but the overall size is not, for example, microtubules $[(\alpha\beta)_n]$.

In general, as used herein, the term multimeric polypeptide complex encompasses all such arrangements.

The term "mature" polypeptide refers to a polypeptide which has undergone a complete, post-translational modification appropriate for the subject polypeptide and the cell of origin.

A "fragment" of a specified polypeptide refers to an amino acid sequence which comprises at least about 3–5 amino acids, more preferably at least about 8–10 amino acids, and even more preferably at least about 15–20 amino acids derived from the specified polypeptide.

"Recombinant host cells," "host cells," "cells," "cell lines," "cell cultures," and other such terms denoting microorganisms or higher eukaryotic cell lines cultured as unicellular entities refer to cells which can be, or have been, used as recipients for recombinant vector or other transferred DNA, and include the original progeny of the original cell which has been transfected.

As used herein "replicon" means any genetic element, such as a plasmid, a chromosome or a virus, that behaves as an autonomous unit of polynucleotide replication within a cell.

A "vector" is a replicon in which another polynucleotide segment is attached, such as to bring about the replication and/or expression of the attached segment.

The term "control sequence" refers to a polynucleotide sequence which is necessary to effect the expression of a coding sequence to which it is ligated. The nature of such control sequences differs depending upon the host organism. In prokaryotes, such control sequences generally include a promoter, a ribosomal binding site and terminators; in eukaryotes, such control sequences generally include promoters, terminators and, in some instances, enhancers. The term "control sequence" thus is intended to include at a minimum all components whose presence is necessary for expression, and also may include additional components whose presence is advantageous, for example, leader sequences.

The term "open reading frame" or "ORF" refers to a region of a polynucleotide sequence which encodes a polypeptide. This region may represent a portion of a coding sequence or a total coding sequence.

A "coding sequence" is a polynucleotide sequence which is transcribed into mRNA and translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to, mRNA, cDNA and recombinant polynucleotide sequences.

The term "immunologically identifiable with/as" refers to the presence of epitope(s) and polypeptide(s) which also are present in and are unique to the designated polypeptide(s). Immunological identity may be determined by antibody binding and/or competition in binding. These techniques are known to the routineer and also are described herein. The uniqueness of an epitope also can be determined by computer searches of known data banks, such as GenBank, for the polynucleotide sequence which encodes the epitope and by amino acid sequence comparisons with other known proteins.

As used herein, "epitope" means an antigenic determinant of a polypeptide or protein. Conceivably, an epitope can comprise three amino acids in a spatial conformation which is unique to the epitope. Generally, an epitope consists of at least five such amino acids and more usually, it consists of at least eight to ten amino acids. Methods of examining spatial conformation are known in the art and include, for example, x-ray crystallography and two-dimensional nuclear magnetic resonance.

A "conformational epitope" is an epitope that is comprised of a specific juxtaposition of amino acids in an immunologically recognizable structure, such amino acids being present on the same polypeptide in a contiguous or non-contiguous order or present on different polypeptides.

A polypeptide is "immunologically reactive" with an antibody when it binds to an antibody due to antibody recognition of a specific epitope contained within the polypeptide. Immunological reactivity may be determined by antibody binding, more particularly, by the kinetics of antibody binding, and/or by competition in binding using as competitor(s) a known polypeptide(s) containing an epitope against which the antibody is directed. The methods for determining whether a polypeptide is immunologically reactive with an antibody are known in the art.

As used herein, the term "immunogenic polypeptide containing an epitope of interest" means naturally occurring polypeptides of interest or fragments thereof, as well as polypeptides prepared by other means, for example, by chemical synthesis or the expression of the polypeptide in a recombinant organism.

The term "transfection" refers to the introduction of an exogenous polynucleotide into a prokaryotic or eucaryotic host cell, irrespective of the method used for the introduction. The term "transfection" refers to both stable and transient introduction of the polynucleotide, and encompasses direct uptake of polynucleotides, transformation, transduction, and f-mating. Once introduced into the host cell, the exogenous polynucleotide may be maintained as a non-integrated replicon, for example, a plasmid, or alternatively, may be integrated into the host genome.

"Treatment" refers to prophylaxis and/or therapy.

The term "individual" as used herein refers to vertebrates, particularly members of the mammalian species and includes, but is not limited to, domestic animals, sports animals, primates and humans; more particularly, the term refers to humans.

The term "test sample" refers to a component of an individual's body which is the source of the analyte (such as antibodies of interest or antigens of interest). These components are well known in the art. A test sample is typically anything suspected of containing a target sequence. Test samples can be prepared using methodologies well known in the art such as by obtaining a specimen from an individual and, if necessary, disrupting any cells contained thereby to release target nucleic acids. These test samples include biological samples which can be tested by the methods of the present invention described herein and include human and animal body fluids such as whole blood, serum, plasma, cerebrospinal fluid, sputum, bronchial washing, bronchial aspirates, urine, lymph fluids, and various external secretions of the respiratory, intestinal and genitourinary tracts, tears, saliva, milk, white blood cells, myelomas and the like; biological fluids such as cell culture supernatants; tissue specimens which may be fixed; and cell specimens which may be fixed.

"Purified product" refers to a preparation of the product which has been isolated from the cellular constituents with which the product is normally associated and from other types of cells which may be present in the sample of interest.

"Analyte," as used herein, is the substance to be detected which may be present in the test sample. The analyte can be any substance for which there exists a naturally occurring specific binding member (such as an antibody), or for which a specific binding member can be prepared. Thus, an analyte is a substance that can bind to one or more specific binding members in an assay. "Analyte" also includes any antigenic substances, haptens, antibodies and combinations thereof. As a member of a specific binding pair, the analyte can be detected by means of naturally occurring specific binding partners (pairs) such as the use of intrinsic factor protein as a member of a specific binding pair for the determination of Vitamin B12, the use of folate-binding protein to determine folic acid, or the use of a lectin as a member of a specific binding pair for the determination of a carbohydrate. The analyte can include a protein, a polypeptide, an amino acid, a nucleotide target and the like. The analyte can be soluble in a body fluid such as blood, blood plasma or serum, urine or the like. The analyte can be in a tissue, either on a cell surface or within a cell. The analyte can be on or in a cell dispersed in a body fluid such as blood, urine, breast aspirate, or obtained as a biopsy sample.

The terms "disease of the reproductive system," "reproductive tissue disease," and "condition of the reproductive system" are used interchangeably herein to refer to any disease or condition of the reproductive tissue including, uterine cancer, cervical cancer, ovarian cancer, breast cancer, cancer of the fallopian tubes, vaginal cancer and endometrial cancer.

"Uterine cancer," as used herein, refers to any malignant disease of the uterus including, but not limited to, endometrioid adenocarcinoma, squamous cell carcinoma, clear cell carcinoma, serous adenocarcinoma, mucinous adenocarcinoma, and undifferentiated carcinoma.

An "Expressed Sequence Tag" or "EST" refers to the partial sequence of a cDNA insert which has been made by reverse transcription of mRNA extracted from a tissue followed by insertion into a vector.

A "transcript image" refers to a table or list giving the quantitative distribution of ESTs in a library and represents the genes active in the tissue from which the library was made.

The present invention provides assays which utilize specific binding members. A "specific binding member," as used herein, is a member of a specific binding pair. That is, two different molecules where one of the molecules, through chemical or physical means, specifically binds to the second molecule. Therefore, in addition to antigen and antibody specific binding pairs of common immunoassays, other specific binding pairs can include biotin and avidin, carbohydrates and lectins, complementary nucleotide sequences, effector and receptor molecules, cofactors and enzymes, enzyme inhibitors, and enzymes and the like. Furthermore, specific binding pairs can include members that are analogs of the original specific binding members, for example, an analyte-analog. Immunoreactive specific binding members include antigens, antigen fragments, antibodies and antibody fragments, both monoclonal and polyclonal and complexes thereof, including those formed by recombinant DNA molecules.

Specific binding members include "specific binding molecules." A "specific binding molecule" intends any specific binding member, particularly an immunoreactive specific binding member. As such, the term "specific binding molecule" encompasses antibody molecules (obtained from both polyclonal and monoclonal preparations), as well as, the following: hybrid (chimeric) antibody molecules (see, for example, Winter, et al., Nature 349: 293–299 (1991), and U.S. Pat. No. 4,816,567); F(ab')$_2$ and F(ab) fragments; Fv molecules (non-covalent heterodimers, see, for example, Inbar, et al., Proc. Natl. Acad. Sci. USA 69: 2659–2662 (1972), and Ehrlich, et al., Biochem. 19: 4091–4096 (1980)); single chain Fv molecules (sFv) (see, for example, Huston, et al., Proc. Natl. Acad. Sci. USA 85: 5879–5883 (1988)); humanized antibody molecules (see, for example, Riechmann, et al., Nature 332: 323–327 (1988), Verhoeyan, et al., Science 239: 1534–1536 (1988), and UK Patent Publication No. GB 2,276,169, published 21 Sep. 1994); and, any functional fragments obtained from such molecules, wherein such fragments retain immunological binding properties of the parent antibody molecule.

The term "hapten," as used herein, refers to a partial antigen or non-protein binding member which is capable of binding to an antibody, but which is not capable of eliciting antibody formation unless coupled to a carrier protein.

A "capture reagent," as used herein, refers to an unlabeled specific binding member which is specific either for the analyte as in a sandwich assay, for the indicator reagent or analyte as in a competitive assay, or for an ancillary specific binding member, which itself is specific for the analyte, as in an indirect assay. The capture reagent can be directly or indirectly bound to a solid phase material before the performance of the assay or during the performance of the assay, thereby enabling the separation of immobilized complexes from the test sample.

The "indicator reagent" comprises a "signal-generating compound" ("label") which is capable of generating and generates a measurable signal detectable by external means, conjugated ("attached") to a specific binding member. In addition to being an antibody member of a specific binding pair, the indicator reagent also can be a member of any specific binding pair, including either hapten-anti-hapten systems such as biotin or anti-biotin, avidin or biotin, a carbohydrate or a lectin, a complementary nucleotide sequence, an effector or a receptor molecule, an enzyme cofactor and an enzyme, an enzyme inhibitor or an enzyme and the like. An immunoreactive specific binding member can be an antibody, an antigen, or an antibody/antigen complex that is capable of binding either to the polypeptide of interest as in a sandwich assay, to the capture reagent as in a competitive assay, or to the ancillary specific binding member as in an indirect assay. When describing probes and probe assays, the term "reporter molecule" may be used. A reporter molecule comprises a signal generating compound as described hereinabove conjugated to a specific binding member of a specific binding pair, such as carbazole or adamantane.

The various "signal-generating compounds" (labels) contemplated include chromagens, catalysts such as enzymes, luminescent compounds such as fluorescein and rhodamine, chemiluminescent compounds such as dioxetanes, acridiniums, phenanthridiniums and luminol, radioactive elements and direct visual labels. Examples of enzymes include alkaline phosphatase, horseradish peroxidase, beta-galactosidase and the like. The selection of a particular label is not critical, but it must be capable of producing a signal either by itself or in conjunction with one or more additional substances.

"Solid phases" ("solid supports") are known to those in the art and include the walls of wells of a reaction tray, test tubes, polystyrene beads, magnetic or non-magnetic beads, nitrocellulose strips, membranes, microparticles such as latex particles, sheep (or other animal) red blood cells and Duracytes® (red blood cells "fixed" by pyruvic aldehyde and formaldehyde, available from Abbott Laboratories, Abbott Park, Ill.) and others. The "solid phase" is not critical and can be selected by one skilled in the art. Thus, latex particles, microparticles, magnetic or non-magnetic beads, membranes, plastic tubes, walls of microtiter wells, glass or silicon chips, sheep (or other suitable animal's) red blood cells and Duracytes® are all suitable examples. Suitable methods for immobilizing peptides on solid phases include ionic, hydrophobic, covalent interactions and the like. A "solid phase," as used herein, refers to any material which is insoluble, or can be made insoluble by a subsequent reaction. The solid phase can be chosen for its intrinsic ability to attract and immobilize the capture reagent. Alternatively, the solid phase can retain an additional receptor which has the ability to attract and immobilize the capture reagent. The additional receptor can include a charged substance that is oppositely charged with respect to the capture reagent itself or to a charged substance conjugated to the capture reagent. As yet another alternative, the receptor molecule can be any specific binding member which is immobilized upon (attached to) the solid phase and which has the ability to immobilize the capture reagent through a specific binding reaction. The receptor molecule enables the indirect binding of the capture reagent to a solid phase material before the performance of the assay or during the performance of the assay. The solid phase thus can be a plastic, derivatized plastic, magnetic or non-magnetic metal, glass or silicon surface of a test tube, microtiter well, sheet, bead, microparticle, chip, sheep (or other suitable animal's) red blood cells, Duracytes® and other configurations known to those of ordinary skill in the art.

It is contemplated and within the scope of the present invention that the solid phase also can comprise any suitable porous material with sufficient porosity to allow access by detection antibodies and a suitable surface affinity to bind antigens. Microporous structures generally are preferred, but materials with a gel structure in the hydrated state may be used as well. Such useful solid supports include, but are not limited to, nitrocellulose and nylon. It is contemplated that such porous solid supports described herein preferably are in the form of sheets of thickness from about 0.01 to 0.5 mm, preferably about 0.1 mm. The pore size may vary within wide limits and preferably is from about 0.025 to 15 microns, especially from about 0.15 to 15 microns. The surface of such supports may be activated by chemical processes which cause covalent linkage of the antigen or antibody to the support. The irreversible binding of the antigen or antibody is obtained, however, in general, by adsorption on the porous material by poorly understood hydrophobic forces. Other suitable solid supports are known in the art.

Reagents.

The present invention provides reagents such as a multimeric polypeptide complex or antigen comprising at least one copy of the EU250 polypeptide (SEQUENCE ID NO:3) sequence, at least one copy of a polypeptide selected from the group consisting of the BU101 polypeptide (SEQUENCE ID NO:2) and the TU104 polypeptide (SEQUENCE ID NO:10), and may also contain one or more unknown polypeptides, and antibodies specific for this multimeric polypeptide complex. The polypeptides, or antibodies of the present invention may be used to provide information leading to the detecting, diagnosing, staging, monitoring, prognosticating, in vivo imaging, preventing or treating of, or determining the predisposition to, diseases and conditions of the reproductive tissue, such as uterine cancer.

Furthermore, the present invention also includes, from a broader viewpoint, uteroglobin complexes (i.e., complexes which comprise 2 or more polypeptide sequences which appear in specific tissues). All such complexes may be used for therapeutic and diagnostic purposes, as described below. For example, in addition to the complex described comprising at least one copy of the EU250 polypeptide, at least one copy of either the BU101 polypeptide or the TU104 polypeptide, as well as possibly one or more other unknown polypeptides, the present invention also encompasses a complex comprising at least one copy of the LU103 polypeptide SEQUENCE ID NO:7) and at least one copy of the LU105 polypeptide (SEQUENCE ID NO:9). This complex may further comprise one or more unknown polypeptides.

The present invention relates to a multimeric polypeptide complex which has components with the deduced amino acid sequences as provided in previous applications, as well as one or more unknown polypeptide sequences, as well as fragments, analogs and derivatives of such a multimeric polypeptide complex. The multimeric polypeptide complex of the present invention may be produced recombinantly, purified from natural sources or synthesized. The fragment, derivative or analog of the multimeric polypeptide complex may be one in which one or more of the amino acid residues of any of the component polypeptide chains is substituted with a conserved or non-conserved amino acid residue (preferably a conserved amino acid residue) and such substituted amino acid residue may or may not be one encoded by the genetic code; or it may be one in which one or more of the amino acid residues includes a substituent group; or it may be one in which any or all of the chains of the multimeric polypeptide complex is fused with another compound, such as a compound to increase the half-life of the multimeric polypeptide complex (for example, polyethylene glycol); or it may be one in which the additional amino acids are fused to any or all of the chains of the multimeric polypeptide complex, such as a leader or secretory sequence or a sequence which is employed for purification of the multimeric polypeptide complex or a proprotein sequence. Such fragments, derivatives and analogs are within the scope of the present invention. The multimeric polypeptide complex of the present invention are provided preferably in an isolated form and preferably purified.

Thus, any chain of the multimeric polypeptide complex of the present invention may have an amino acid sequence that is identical to that of the naturally occurring polypeptide or that is different by minor variations due to one or more amino acid substitutions. The variation may be a "conservative change" wherein the substituted amino acid has similar structural or chemical properties, e.g., replacement of leucine with isoleucine or threonine with serine. In contrast, variations may include nonconservative changes, e.g., replacement of a glycine with a tryptophan. Similar minor variations may also include amino acid deletions or insertions, or both. Guidance in determining which and how many amino acid residues may be substituted, inserted or deleted without changing biological or immunological activity may be found using computer programs well known in the art, for example, DNASTAR software (DNASTAR Inc., Madison Wis.).

Thus, a multimeric polypeptide complex of the present invention may have a composition comprising at least one copy of the EU250 sequence ($\beta$) and at least one copy of the BU101 sequence ($\alpha$) and/or at least one copy of the TU104 sequence ($\gamma$). The complex may or may not also have at least one copy of unknown sequences, $\alpha'$, $\beta'$ or $\gamma$. These components may be present in any ratio.

This invention also provides teachings as to the production of the polypeptides provided herein.

Drug Screening.

The present invention provides a method of screening a plurality of compounds for specific binding to the multimeric polypeptide complex, or any fragment thereof, to identify at least one compound which specifically binds the multimeric polypeptide complex. Such a method comprises the steps of providing at least one compound; combining the multimeric polypeptide complex with each compound under suitable conditions for a time sufficient to allow binding; and detecting the multimeric polypeptide complex binding to each compound.

The polypeptide complex, polypeptides, or peptide fragment(s) employed in such a test may either be free in solution, affixed to a solid support, borne on a cell surface or located intracellularly. One method of screening utilizes eukaryotic or prokaryotic host cells which are stably transfected with recombinant nucleic acids which can express the polypeptide complex, polypeptide or peptide fragment. A drug, compound, or any other agent may be screened against such transfected cells in competitive binding assays. For example, the formation of complexes between a polypeptide and the agent being tested can be measured in either viable or fixed cells.

The present invention thus provides methods of screening for drugs, compounds, or any other agent which can be used to treat diseases associated with the multimeric polypeptide complex. These methods comprise contacting the agent with a polypeptide complex, polypeptide or fragment thereof and assaying for either the presence of a complex between the agent and the polypeptide, or for the presence of a complex between the polypeptide and the cell. In competitive binding assays, the polypeptide typically is labeled. After suitable incubation, free (or uncomplexed) polypeptide or fragment thereof is separated from that present in bound form, and the amount of free or uncomplexed label is used as a measure of the ability of the particular agent to bind to the polypeptide or to interfere with the polypeptide/cell complex.

The present invention also encompasses the use of competitive screening assays in which neutralizing antibodies capable of binding polypeptide specifically compete with a test agent for binding to the polypeptide complex, polypeptide or fragment thereof. In this manner, the antibodies can be used to detect the presence of any polypeptide in the test sample which shares one or more antigenic determinants with a multimeric polypeptide complex as provided herein.

Another technique for screening provides high throughput screening for compounds having suitable binding affinity to at least one polypeptide of the multimeric polypeptide complex disclosed herein. Briefly, large numbers of different small peptide test compounds are synthesized on a solid phase, such as plastic pins or some other surface. The peptide test compounds are reacted with polypeptide and washed. Polypeptide thus bound to the solid phase is detected by methods well-known in the art. Purified polypeptide can also be coated directly onto plates for use in the screening techniques described herein. In addition, non-neutralizing antibodies can be used to capture the polypeptide and immobilize it on the solid support. See, for example, EP 84/03564, published on Sep. 13, 1984, which is incorporated herein by reference.

The goal of rational drug design is to produce structural analogs of biologically active polypeptides of interest or of the small molecules including agonists, antagonists, or inhibitors with which they interact. Such structural analogs can be used to design drugs which are more active or stable forms of the polypeptide or which enhance or interfere with the function of a polypeptide in vivo. J. Hodgson, Bio/Technology 9: 19–21 (1991), incorporated herein by reference.

For example, in one approach, the three-dimensional structure of a polypeptide, or of a polypeptide-inhibitor complex, is determined by x-ray crystallography, by computer modeling or, most typically, by a combination of the two approaches. Both the shape and charges of the polypeptide must be ascertained to elucidate the structure and to determine active site(s) of the molecule. Less often, useful information regarding the structure of a polypeptide may be gained by modeling based on the structure of homologous proteins. In both cases, relevant structural information is used to design analogous polypeptide-like molecules or to identify efficient inhibitors.

Useful examples of rational drug design may include molecules which have improved activity or stability as shown by S. Braxton et al., Biochemistry 31: 7796–7801 (1992), or which act as inhibitors, agonists, or antagonists of native peptides as shown by S .B. P. Athauda et al., J. Biochem. (Tokyo) 113 (6): 742–746 (1993), incorporated herein by reference.

It also is possible to isolate a target-specific antibody selected by an assay as described hereinabove, and then to determine its crystal structure. In principle this approach yields a pharmacophore upon which subsequent drug design can be based. It further is possible to bypass protein crystallography altogether by generating anti-idiotypic antibodies ("anti-ids") to a functional, pharmacologically active antibody. As a mirror image of a mirror image, the binding site of the anti-id is an analog of the original receptor. The anti-id then can be used to identify and isolate peptides from banks of chemically or biologically produced peptides. The isolated peptides then can act as the pharmacophore (that is, a prototype pharmaceutical drug).

A sufficient amount of a recombinant polypeptide complex of the present invention may be made available to perform analytical studies such as X-ray crystallography. In addition, knowledge of the polypeptide amino acid sequences which are derivable from the nucleic acid sequences will provide guidance to those employing computer modeling techniques in place of, or in addition to, x-ray crystallography.

Antibodies specific to a multimeric polypeptide complex (e.g., anti-multimeric polypeptide complex antibodies) further may be used to inhibit the biological action of the polypeptide complex by binding to the polypeptide complex. In this manner, the antibodies may be used in therapy, for example, to treat breast tissue diseases including breast cancer and its metastases.

Further, such antibodies can detect the presence or absence of a multimeric polypeptide complex in a test sample and, therefore, are useful as diagnostic markers for the diagnosis of a reproductive tissue disease or condition especially uterine cancer. Such antibodies may also function as a diagnostic marker for reproductive tissue disease conditions, such as uterine cancer.

The present invention also is directed to antagonists and inhibitors of the polypeptides of the present invention. The antagonists and inhibitors are those which inhibit or eliminate the function of the polypeptide complex. Thus, for example, an antagonist may bind to a polypeptide of the present invention and inhibit or eliminate its function. The antagonist, for example, could be an antibody against the polypeptide which eliminates the activity of a multimeric polypeptide complex by binding a polypeptide, or in some cases the antagonist may be an oligonucleotide. Examples of small molecule inhibitors include, but are not limited to, small peptides or peptide-like molecules.

The antagonists and inhibitors may be employed as a composition with a pharmaceutically acceptable carrier including, but not limited to, saline, buffered saline, dextrose, water, glycerol, ethanol and combinations thereof. Administration of multimeric polypeptide complex inhibitors is preferably systemic. The present invention also provides an antibody which inhibits the action of such a polypeptide complex.

Recombinant Technology

The present invention provides host cells and expression vectors for the co-expression of EU250 polypeptide (SEQUENCE ID NO:3) and a polypeptide selected from the group consisting of the BU101 polypeptide (SEQUENCE ID NO:2) and the TU104 polypeptide (SEQUENCE ID NO:10), and possibly unknown α' and/or β' and/or γ' polypeptides; and methods for the production of the multimeric polypeptide complex they encode. Such methods comprise culturing the host cells under conditions suitable for the expression of the 1) EU250 polypeptide (SEQUENCE ID NO:3) and the 2) BU101 polypeptide (SEQUENCE ID NO:2) and/or the TU104 polypeptide (SEQUENCE ID NO:10), and 3) unknown α' and/or β' and/or γ' polypeptides, and recovering the multimeric polypeptide(s) and/or multimeric polypeptide complex from the cell culture.

The present invention also provides vectors which individually encode EU250, BU101, TU104, and unknown α' and/or β' and/or γ' polypeptide(s) of the present invention; host cells which are genetically engineered with vectors of the present invention; and, the production of all, or any, of the subunits of the multimeric polypeptide complex of the present invention by recombinant techniques.

Host cells are genetically engineered (transfected, transduced or transformed) with vectors which may be cloning vectors or expression vectors. The vector may be in the form of a plasmid, a viral particle, a phage, etc. The engineered host cells can be cultured in conventional nutrient media modified as appropriate for activating promoters, selecting transfected cells, or amplifying EU250 (SEQUENCE ID NO:4), BU101 (SEQUENCE ID NO:1), TU104

(SEQUENCE ID NO:5), or unknown α' and/or β' and/or γ' gene(s). The culture conditions, such as temperature, pH and the like, are those previously used with the host cell selected for expression, and will be apparent to the ordinarily skilled artisan.

The polynucleotides may be employed for producing a polypeptide or polypeptide complex(es) by recombinant techniques. Thus, the polynucleotide sequence may be included in any one of a variety of expression vehicles, in particular, vectors or plasmids for expressing a polypeptide. Such vectors include chromosomal, nonchromosomal and synthetic DNA sequences, e.g., derivatives of SV40; bacterial plasmids; phage DNA; yeast plasmids; vectors derived from combinations of plasmids and phage DNA, viral DNA such as vaccinia, adenovirus, fowl pox virus and pseudorabies. However, any other plasmid or vector may be used so long as it is replicable and viable in the host.

The appropriate DNA sequence may be inserted into the vector by a variety of procedures. In general, the DNA sequence is inserted into appropriate restriction endonuclease sites by procedures known in the art. Such procedures and others are deemed to be within the scope of those skilled in the art. The DNA sequence in the expression vector is operatively linked to an appropriate expression control sequence(s) (promoter) to direct mRNA synthesis. Representative examples of such promoters include, but are not limited to, the LTR or the SV40 promoter, the *E. coli* lac or trp, the phage lambda P sub L promoter and other promoters known to control expression of genes in prokaryotic or eukaryotic cells or their viruses. The expression vector also contains a ribosome binding site for translation initiation and a transcription terminator. The vector may also include appropriate sequences for amplifying expression. In addition, the expression vectors preferably contain a gene to provide a phenotypic trait for selection of transfected host cells such as dihydrofolate reductase or neomycin resistance for eukaryotic cell culture, or such as tetracycline or ampicillin resistance in *E. coli*.

The vector containing the appropriate DNA sequence as hereinabove described, as well as an appropriate promoter or control sequence, may be employed to transfect an appropriate host to permit the host to express the protein. As representative examples of appropriate hosts, there may be mentioned: bacterial cells, such as *E. coli, Salmonella typhimurium; Streptomyces* sp.; fungal cells, such as yeast; insect cells, such as *Drosophila* and Sf9; animal cells, such as CHO, COS or Bowes melanoma; plant cells, etc. The selection of an appropriate host is deemed to be within the scope of those skilled in the art from the teachings provided herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences including, for example, a promoter, operably linked to the sequence. Large numbers of suitable vectors and promoters are known to those of skill in the art and are commercially available. The following vectors are provided by way of example. Bacterial: pINCY (Incyte Pharmaceuticals Inc., Palo Alto, Calif.), pSPORT1 (Life Technologies, Gaithersburg, Md.), pQE70, pQE60, pQE-9 (Qiagen) pBs, phagescript, psiX174, pBluescript SK, pBsKS, pNH8a, pNH16a, pNH18a, pNH46a (Stratagene); pTrc99A, pKK223-3, pKK233-3, pDR540, pRIT5 (Pharmacia); Eukaryotic: pWLneo, pSV2cat, pOG44, pXT1, pSG (Stratagene) pSVK3, pBPV, pMSG, pSVL (Pharmacia). However, any other plasmid or vector may be used as long as it is replicable and viable in the host.

Plasmid pINCY is generally identical to the plasmid pSPORT1 (available from Life Technologies, Gaithersburg, Md.) with the exception that it has two modifications in the polylinker (multiple cloning site). These modifications are (1) it lacks a HindIII restriction site and (2) its EcoRI restriction site lies at a different location. pINCY is created from pSPORT1 by cleaving pSPORT1 with both HindIII and EcoRI and replacing the excised fragment of the polylinker with synthetic DNA fragments (SEQUENCE ID NOS:11–12). This replacement may be made in any manner known to those of ordinary skill in the art. For example, the two nucleotide sequences, SEQUENCE ID NOS:11–12, may be generated synthetically with 5' terminal phosphates, mixed together, and then ligated under standard conditions for performing staggered end ligations into the pSPORT1 plasmid cut with HindIII and EcoRI. Suitable host cells (such as *E. coli* DH5α cells) then are transfected with the ligated DNA and recombinant clones are selected for ampicillin resistance. Plasmid DNA then is prepared from individual clones and subjected to restriction enzyme analysis or DNA sequencing in order to confirm the presence of insert sequences in the proper orientation. Other cloning strategies known to the ordinary artisan also may be employed.

Promoter regions can be selected from any desired gene using CAT (chloramphenicol transferase) vectors or other vectors with selectable markers. Two appropriate vectors are pKK232-8 and pCM7. Particular named bacterial promoters include lac, lacZ, T3, SP6, T7, gpt, lambda P sub R, P sub L and trp. Eukaryotic promoters include cytomegalovirus (CMV) immediate early, herpes simplex virus (HSV) thymidine kinase, early and late SV40, LTRs from retroviruses and mouse metallothionein-I. Selection of the appropriate vector and promoter is well within the level of ordinary skill in the art.

In a further embodiment, the present invention provides host cells containing the above-described construct. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation [L. Davis et al., Basic Methods in Molecular Biology, 2nd edition, Appleton and Lang, Paramount Publishing, East Norwalk, Conn. (1994)].

The constructs in host cells can be used in a conventional manner to produce the gene product encoded by the recombinant sequence. Alternatively, the polypeptides of the invention can be synthetically produced by conventional peptide synthesizers.

Recombinant proteins can be expressed in mammalian cells, yeast, bacteria, or other cells, under the control of appropriate promoters. Cell-free translation systems can also be employed to produce such proteins using RNAs derived from the DNA constructs. Appropriate cloning and expression vectors for use with prokaryotic and eukaryotic hosts are described by Sambrook et al., Molecular Cloning: A Laboratory Manual, Second Edition, (Cold Spring Harbor, N.Y., 1989), which is hereby incorporated by reference.

Transcription of a DNA encoding the polypeptide(s) of the present invention by higher eukaryotes is increased by inserting an enhancer sequence into the vector. Enhancers are cis-acting elements of DNA, usually about from 10 to 300 bp, that act on a promoter to increase its transcription. Examples include the SV40 enhancer on the late side of the replication origin (bp 100 to 0.270), a cytomegalovirus early promoter enhancer, a polyoma enhancer on the late side of the replication origin and adenovirus enhancers.

Generally, recombinant expression vectors will include origins of replication and selectable markers permitting transfection of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), alpha factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transfection include *E. coli, Bacillus subtilis, Salmonella typhimurium* and various species within the genera *Pseudomonas, Streptomyces* and *Staphylococcus*, although others may also be employed as a routine matter of choice.

Useful expression vectors for bacterial use comprise a selectable marker and bacterial origin of replication derived from plasmids comprising genetic elements of the well-known cloning vector pBR322 (ATCC 37017). Other vectors include but are not limited to PKK223-3 (Pharmacia Fine Chemicals, Uppsala, Sweden) and GEM1 (Promega Biotec, Madison, Wis.). These pBR322 "backbone" sections are combined with an appropriate promoter and the structural sequence to be expressed.

Following transfection of a suitable host and growth of the host to an appropriate cell density, the selected promoter is derepressed by appropriate means (e.g., temperature shift or chemical induction), and cells are cultured for an additional period. Cells are typically harvested by centrifugation, disrupted by physical or chemical means, and the resulting crude extract retained for further purification. Microbial cells employed in expression of proteins can be disrupted by any convenient method including freeze-thaw cycling, sonication, mechanical disruption, or use of cell lysing agents. Such methods are well-known to the ordinary artisan.

Various mammalian cell culture systems can also be employed to express recombinant protein. Examples of mammalian expression systems include the COS-7 lines of monkey kidney fibroblasts described by Gluzman, Cell 23: 175 (1981), and other cell lines capable of expressing a compatible vector, such as the C127, HEK-293, 3T3, CHO, HeLa and BHK cell lines. Mammalian expression vectors will comprise an origin of replication, a suitable promoter and enhancer and also any necessary ribosome binding sites, polyadenylation sites, splice donor and acceptor sites, transcriptional termination sequences and 5' flanking nontranscribed sequences. DNA sequences derived from the SV40 viral genome, for example, SV40 origin, early promoter, enhancer, splice, and polyadenylation sites may be used to provide the required nontranscribed genetic elements. Representative, useful vectors include pRc/CMV and pcDNA3 (available from Invitrogen, San Diego, Calif.).

Polypeptides are recovered and purified from recombinant cell cultures by known methods including affinity chromatography, ammonium sulfate or ethanol precipitation, acid extraction, anion or cation exchange chromatography, phosphocellulose chromatography, hydrophobic interaction chromatography, hydroxyapatite chromatography or lectin chromatography. It is preferred to have low concentrations (approximately 0.1–5 mM) of calcium ion present during purification [Price, et al., J. Biol. Chem. 244: 917 (1969)]. Protein refolding steps can be used, as necessary, in completing configuration of the polypeptide. Finally, high performance liquid chromatography (HPLC) can be employed for final purification steps.

Thus, polypeptides of the present invention may be naturally purified products expressed from a high expressing cell line, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated with mammalian or other eukaryotic carbohydrates or may be non-glycosylated. The polypeptides of the invention may also include a methionine residue as initial amino acid.

Plasmids containing cDNAs can be constructed from available plasmids in accord with published, known procedures. In addition, equivalent plasmids to those described are known in the art and will be apparent to one of ordinary skill in the art. The cDNA can be shuttled into other vectors known to be useful for expression of protein in specific hosts. Oligonucleotide primers containing cloning sites and segments of DNA sufficient to hybridize to stretches at both ends of the target cDNA can be synthesized chemically by standard methods. These primers can then be used to amplify the desired gene segments by PCR. The resulting new gene segments can be digested with appropriate restriction enzymes under standard conditions and isolated by gel electrophoresis. Alternately, similar gene segments can be produced by digestion of the cDNA with appropriate restriction enzymes and filling in the missing gene segments with chemically synthesized oligonucleotides. Segments of the coding sequence from more than one gene can be ligated together and cloned in appropriate vectors to optimize expression of recombinant sequence.

Suitable expression hosts for such chimeric molecules include, but are not limited to, mammalian cells, such as Chinese Hamster Ovary (CHO) and human embryonic kidney (HEK) 293 cells, insect cells, such as Sf9 cells, yeast cells, such as *Saccharomyces cerevisiae* and bacteria, such as *E. coli*. For each of these cell systems, a useful expression vector may also include an origin of replication to allow propagation in bacteria and a selectable marker such as the beta-lactamase antibiotic resistance gene to allow selection in bacteria. In addition, the vectors may include a second selectable marker, such as the neomycin phosphotransferase gene, to allow selection in transfected eukaryotic host cells. Vectors for use in eukaryotic expression hosts may require the addition of 3' poly A tail if the sequence of interest lacks poly A.

Additionally, the vector may contain promoters or enhancers which increase gene expression. Such promoters are host specific and include, but are not limited to, MMTV, SV40, or metallothionine promoters for CHO cells; trp, lac, tac or T7 promoters for bacterial hosts; or alpha factor, alcohol oxidase or PGH promoters for yeast. Adenoviral vectors with or without transcription enhancers, such as the Rous sarcoma virus (RSV) enhancer, may be used to drive protein expression in mammalian cell lines. Once homogeneous cultures of recombinant cells are obtained, large quantities of recombinantly produced protein can be recovered from the conditioned medium and analyzed using chromatographic methods well known in the art. An alternative method for the production of large amounts of secreted protein involves the transfection of mammalian embryos and the recovery of the recombinant protein from milk produced by transgenic cows, goats, sheep, etc. Polypeptides and closely related molecules may be expressed recombinantly in such a way as to facilitate protein purification. One approach involves expression of a chimeric protein which includes one or more additional polypeptide domains not naturally present on human polypeptides. Such purification-facilitating domains include, but are not limited to, metal-chelating peptides such as histidine-tryptophan domains that allow purification on immobilized metals, protein A domains that allow purification on immobilized immunoglobulin and the domain utilized in the FLAGS extension/affinity purification system (Immunex Corp, Seattle, Wash.). The inclusion of a cleavable linker sequence such as Factor Xa or enterokinase from Invitrogen (San Diego, Calif.) between the polypeptide sequence and the purification domain may be useful for recovering the polypeptide.

Immunoassays.

Polypeptides, multimeric polypeptide complexes, including fragments, derivatives, and analogs thereof, or cells expressing such polypeptides or multimeric polypeptide complexes, can be utilized in a variety of assays, many of which are described herein, for the detection of antibodies to breast tissue. They also can be used as immunogens to produce antibodies. These antibodies can be, for example, polyclonal or monoclonal antibodies, chimeric, single chain and humanized antibodies, as well as Fab fragments, or the product of an Fab expression library. Various procedures known in the art may be used for the production of such antibodies and fragments.

For example, antibodies generated against a multimeric polypeptide complex can be obtained by direct injection of the multimeric polypeptide complex into an animal or by administering the multimeric polypeptide complex to an animal such as a mouse, rabbit, goat or human. A mouse, rabbit or goat is preferred. The multimeric polypeptide complex is composed of a group of sequences consisting of EU250 (SEQUENCE ID NO:3), BU101 (SEQUENCE ID NO:2), TU104 (SEQUENCE ID NO:10), and unknown α' and/or β' and/or γ' polypeptide(s), and fragments thereof. The antibody so obtained then binds the multimeric polypeptide complex itself. In this manner, a sequence encoding only a fragment of the multimeric polypeptide complex or any of its component polypeptides can be used to generate antibodies that bind the native polypeptide complex. Such antibodies then can be used to isolate the multimeric polypeptide complex from test samples such as tissue suspected of containing that multimeric polypeptide complex. For preparation of monoclonal antibodies, any technique which provides antibodies produced by continuous cell line cultures can be used. Examples include the hybridoma technique as described by Kohler and Milstein, Nature 256: 495–497 (1975), the trioma technique, the human B-cell hybridoma technique as described by Kozbor et al., Immun. Today 4: 72 and the EBV-hybridoma technique to produce human monoclonal antibodies as described by Cole et al., in Monoclonal Antibodies and Cancer Therapy, Alan R. Liss, Inc, New York, N.Y., pp. 77–96 (1985). Techniques described for the production of single chain antibodies can be adapted to produce single chain antibodies to immunogenic polypeptide products of this invention. See, for example, U.S. Pat. No. 4,946,778, which is incorporated herein by reference.

The monoclonal antibodies or fragments thereof can be provided individually to detect antigens of the multimeric polypeptide complex. Combinations of the monoclonal antibodies (and fragments thereof) provided herein also may be used together as components in a mixture or "cocktail" wherein at least one antibody which binds to the multimeric polypeptide complex of the invention, along with antibodies which specifically bind to other regions of the multimeric polypeptide complex are present, each antibody having different binding specificities. For example, one monoclonal antibody may recognize a shared epitope wherein that epitope is derived from components of two or more different polypeptides. In this case, the epitope would be specific for a multimeric complex wherein the polypeptides were present but would not bind to the individual, isolated polypeptides. Another monoclonal antibody may recognize an epitope specified within a single polypeptide sequence. In this case, the epitope may be present in both the individual, isolated polypeptide as well as in the multimeric polypeptide complex. Another monoclonal antibody may recognize an epitope specified within a single polypeptide sequence. In this case, the epitope may be present in the individual, isolated polypeptide but not in the multimeric polypeptide complex. The epitope may be buried or be conformationally distinct as a result of complexation with other polypeptides. Thus, this cocktail can include the monoclonal antibodies of the invention which are directed to any single antigenic determinant of the multimeric polypeptides disclosed herein and other monoclonal antibodies specific to other antigenic determinants of these antigens or other related proteins.

The polyclonal antibody or fragment thereof which can be used in the assay formats should specifically bind to the multimeric polypeptide complex of the present invention or any of the component polypeptides of this complex, or fragments thereof, additionally used in the assay. The polyclonal antibody used preferably is of mammalian origin such as, human, goat, rabbit or sheep polyclonal antibody which binds the multimeric polypeptide complex. Most preferably, the polyclonal antibody is of rabbit origin. The polyclonal antibodies used in the assays can be used either alone or as a cocktail of polyclonal antibodies. Since the cocktails used in the assay formats are comprised of either monoclonal antibodies or polyclonal antibodies having different binding specificity to the multimeric polypeptide complex, they are useful for the detecting, diagnosing, staging, monitoring, prognosticating, in vivo imaging, preventing or treating, or determining the predisposition to, diseases and conditions of the breast, such as breast cancer.

Various assay formats may utilize the antibodies of the present invention, including "sandwich" immunoassays. For example, the antibodies of the present invention, or fragments thereof, can be employed in various assay systems to determine the presence, if any, of the multimeric polypeptide antigen in a test sample. For example, in a first assay format, a polyclonal or monoclonal antibody or fragment thereof, or a combination of these antibodies, which has been coated on a solid phase, is contacted with a test sample, to form a first mixture. This first mixture is incubated for a time and under conditions sufficient to form antigen/antibody complexes. Then, an indicator reagent comprising a monoclonal or a polyclonal antibody or a fragment thereof, or a combination of these antibodies, to which a signal generating compound has been attached, is contacted with the antigen/antibody complexes to form a second mixture. This second mixture then is incubated for a time and under conditions sufficient to form antibody/antigen/antibody complexes. The presence of antigen in the test sample and captured on the solid phase, if any, is determined by detecting the measurable signal generated by the signal generating compound. The amount of antigen present in the test sample is proportional to the signal generated.

In another example of a sandwich immunoassay, the antibodies of the present invention, or fragments thereof, can be employed in various assay systems to determine the presence, if any, of the individual, isolated polypeptides that constitute the multimeric polypeptide complex. In this case, the antibodies utilized bind to an epitope that is present in the individual, isolated polypeptide but is not available for binding in the multimeric polypeptide complex.

In another example of a sandwich immuoassay, the antibodies of the present invention, or fragments thereof, can be employed in various assay systems to determine the presence, if any, of both the individual, isolated polypeptides that constitute the multimeric polypeptide complex and the multimeric polypeptide complex itself. In this case, the antibodies utilized bind to an epitope that is present in the individual, isolated polypeptide and in the multimeric polypeptide complex. Measurements of these different antigens, specifically, the multimeric polypeptide complex (bound), the individual, isolated polypeptides (free), and both the multimeric polypeptide complex and the individual, isolated polypeptides (total), and ratios thereof, may be useful for the detecting, diagnosing, staging, monitoring, prognosticating, in vivo imaging, preventing or treating, or determining the predisposition to diseases and conditions of the reproductive tissue, such as uterine cancer or breast cancer. See, for example, International Publication Number WO 92/01936, which is incorporated herein by reference.

In an alternative assay format, a mixture is formed by contacting: (1) a polyclonal antibody, monoclonal antibody, or fragment thereof, which specifically binds to a multimeric polypeptide antigen and/or one of its component polypeptide chains such that measurements of free, bound, or total can be made, or a combination of such antibodies bound to a solid support; (2) the test sample; and (3) an indicator reagent comprising a monoclonal antibody, polyclonal antibody, or fragment thereof, which specifically binds to a different epitope of the multimeric polypeptide antigen and/or one of its component chains (or a combination of these antibodies) to which a signal generating compound is attached. This mixture is incubated for a time and under conditions sufficient to form antibody/antigen/antibody complexes. The presence, if any, of the multimeric polypeptide antigen and/or one of its component polypeptide chains present in the test sample and captured on the solid phase is determined by detecting the measurable signal generated by the signal generating compound. The amount of antigen present in the test sample is proportional to the signal generated.

In another assay format, antibodies coated on solid phases or labeled with detectable labels are then allowed to compete with those present in a patient sample (if any) for a limited amount of antigen. A reduction in binding of the polyclonal or monoclonal antibodies is an indication of the presence of antigen in the patient sample. The presence of antibodies against the antigen indicates the presence of breast tissue disease, especially breast cancer, in the patient.

In yet another detection method, each of the monoclonal or polyclonal antibodies of the present invention can be employed in the detection of multimeric polypeptide antigens including the multimeric polypeptide complex and/or one of its component polypeptide chains in tissue sections, as well as in cells, by immunohistochemical analysis. The tissue sections can be cut from either frozen or chemically fixed samples of tissue. If the antigens are to be detected in cells, the cells can be isolated from blood, urine, tissue, or other bodily fluids. The cells may be obtained by biopsy, either surgical or by needle. The cells can be isolated by centrifugation or magnetic attraction after labeling with magnetic particles or ferrofluids so as to enrich a particular fraction of cells for staining with the antibodies of the present invention. Cytochemical analysis wherein these antibodies are labeled directly (with, for example, fluorescein, colloidal gold, horseradish peroxidase, alkaline phosphatase, etc.) or are labeled by using secondary labeled anti-species antibodies (with various labels as exemplified herein) to track the histopathology of disease also are within the scope of the present invention.

In addition, these monoclonal antibodies can be bound to matrices similar to CNBr-activated Sepharose and used for the affinity purification of the multimeric polypeptide complex and/or one of its component chains from cell cultures or biological tissues such as to purify recombinant and native protein.

The monoclonal antibodies of the invention also can be used for the generation of chimeric antibodies for therapeutic use, or other similar applications.

It is contemplated and within the scope of the present invention that the multimeric polypeptide antigen may be detectable in assays by use of a recombinant antigen as well as by use of a synthetic peptide or purified peptide, which peptide comprises an amino acid sequence of any component polypeptide chain of the multimeric polypeptide complex. The amino acid sequence of such a polypeptide is selected from the group consisting of EU250 polypeptide (SEQUENCE ID NO:3), BU101 polypeptide (SEQUENCE ID NO:2), TU104 polypeptide (SEQUENCE ID NO:10), an unknown $\alpha'$, $\beta'$, and $\gamma'$ polypeptide sequence, and fragments thereof. It also is within the scope of the present invention that different synthetic, recombinant or purified peptides, identifying different epitopes of the multimeric polypeptide complex, can be used in combination in an assay for the detecting, diagnosing, staging, monitoring, prognosticating, in vivo imaging, preventing or treating, or determining the predisposition to diseases and conditions of the reproductive tissue, such as uterine cancer. In this case, all of these peptides or polypeptides can be coated onto one solid phase; or each separate peptide or polypeptide may be coated onto separate solid phases, such as microparticles, and then combined to form a mixture of peptides or polypeptides which can be later used in assays. Furthermore, it is contemplated that multiple peptides or polypeptides which define epitopes from different antigens may be used for the detection, diagnosis, staging, monitoring, prognosis, prevention or treatment of, or determining the predisposition to, diseases and conditions of the reproductive tissue, such as uterine cancer. Peptides or polypeptides coated on solid phases or labeled with detectable labels are then allowed to compete with those present in a patient sample (if any) for a limited amount of antibody. A reduction in binding of the synthetic, recombinant, or purified peptides to the antibody (or antibodies) is an indication of the presence of the multimeric polypeptide antigen in the patient sample. The presence of the multimeric polypeptide antigen indicates the presence of reproductive tissue disease, especially uterine cancer, in the patient. Variations of assay formats are known to those of ordinary skill in the art and many are discussed herein below.

In another assay format, one or a combination of at least two polypeptides, peptides, or the multimeric polypeptide complex of the invention can be employed as a competitive probe for the detection of the multimeric polypeptide antigen. For example, antibodies to the multimeric polypeptide complex such as the monoclonal and polyclonal antibodies disclosed herein, either alone or in combination, are coated on a solid phase. A test sample suspected of containing the multimeric polypeptide antigen then is incubated with an indicator reagent comprising a signal generating compound and at least one monoclonal antibody of the invention for a time and under conditions sufficient to form antigen/antibody complexes of either the test sample and indicator reagent bound to the solid phase or the indicator reagent bound to the solid phase. The reduction in binding of the monoclonal antibody to the solid phase can be quantitatively measured.

In another assay format, the presence of anti-multimeric polypeptide antibody and/or multimeric polypeptide antigen can be detected in a simultaneous assay, as follows. A test sample is simultaneously contacted with a capture reagent of a first analyte, wherein said capture reagent comprises a first binding member specific for a first analyte attached to a solid phase and a capture reagent for a second analyte, wherein said capture reagent comprises a first binding member for a second analyte attached to a second solid phase, to thereby form a mixture. This mixture is incubated for a time and under conditions sufficient to form capture reagent/first analyte and capture reagent/second analyte complexes. These so-formed complexes then are contacted with an indicator reagent comprising a member of a binding pair specific for the first analyte labeled with a signal generating compound and an indicator reagent comprising a member of a binding pair specific for the second analyte labeled with a signal generating compound to form a second mixture. This second mixture is incubated for a time and under conditions sufficient to form capture reagent/first analyte/indicator reagent complexes and capture reagent/second analyte/indicator reagent complexes. The presence of one or more analytes is determined by detecting a signal generated in connection with the complexes formed on either or both solid phases as an indication of the presence of one or more analytes in the test sample. In this assay format, recombinant antigens derived from the expression systems disclosed herein may be utilized, as well as monoclonal antibodies produced from the proteins derived from the expression systems as disclosed herein. For example, in this assay system, the multimeric polypeptide antigen can be the first analyte. Such assay systems are described in greater detail in EP Publication No. 0473065.

In yet other assay formats, the polypeptides disclosed herein may be utilized to detect the presence of antibody against the multimeric polypeptide antigen in test samples. For example, a test sample is incubated with a solid phase to which at least one polypeptide such as a recombinant protein or synthetic peptide has been attached. The polypeptide is selected from the group consisting of EU250 (SEQUENCE ID NO:3), BU101 (SEQUENCE ID NO:2), TU104 (SEQUENCE ID NO:10), α' polypeptide, β' polypeptide, γ' polypeptide, and fragments thereof. These are reacted for a time and under conditions sufficient to form antigen/antibody complexes. Following incubation, the antigen/antibody complex is detected. Indicator reagents may be used to facilitate detection, depending upon the assay system chosen.

In another assay format, a test sample is contacted with a solid phase to which a recombinant protein produced as described herein is attached, and also is contacted with a monoclonal or polyclonal antibody specific for the protein, which preferably has been labeled with an indicator reagent. After incubation for a time and under conditions sufficient for antibody/antigen complexes to form, the solid phase is separated from the free phase, and the label is detected in either the solid or free phase as an indication of the presence of antibody against the multimeric polypeptide antigen.

Other assay formats utilizing the recombinant antigens disclosed herein are contemplated. These include contacting a test sample with a solid phase to which at least one antigen from a first source has been attached, incubating the solid phase and test sample for a time and under conditions sufficient to form antigen/antibody complexes, and then contacting the solid phase with a labeled antigen, which antigen is derived from a second source different from the first source. For example, a recombinant protein derived from a first source such as E. coli is used as a capture antigen on a solid phase, a test sample is added to the so-prepared solid phase, and following standard incubation and washing steps as deemed or required, a recombinant protein derived from a different source (i.e., non-E. coli) is utilized as a part of an indicator reagent which subsequently is detected. Likewise, combinations of a recombinant antigen on a solid phase and synthetic peptide in the indicator phase also are possible. Any assay format which utilizes an antigen specific for the multimeric polypeptide complex produced or derived from a first source as the capture antigen and an antigen specific for the multimeric polypeptide complex from a different second source is contemplated. Thus, various combinations of recombinant antigens, as well as the use of synthetic peptides, purified proteins and the like, are within the scope of this invention. Assays such as this and others are described in U.S. Pat. No. 5,254,458, which enjoys common ownership and is incorporated herein by reference.

Other embodiments which utilize various other solid phases also are contemplated and are within the scope of this invention. For example, ion capture procedures for immobilizing an immobilizable reaction complex with a negatively charged polymer (described in EP publication No. 0 326 100 and EP publication No. 0 406 473), can be employed according to the present invention to effect a fast solution-phase immunochemical reaction. An immobilizable immune complex is separated from the rest of the reaction mixture by ionic interactions between the negatively charged poly-anion/immune complex and the previously treated, positively charged porous matrix and detected by using various signal generating systems previously described, including those described in chemiluminescent signal measurements as described in EPO Publication No. 0273,115.

Also, the methods of the present invention can be adapted for use in systems which utilize microparticle technology including automated and semi-automated systems wherein the solid phase comprises a microparticle (magnetic or non-magnetic). Such systems include those described in, for example, published EPO applications Nos. EP 0 425 633 and EP 0 424 634, respectively.

The use of scanning probe microscopy (SPM) for immunoassays also is a technology to which the monoclonal antibodies of the present invention are easily adaptable. In scanning probe microscopy, particularly in atomic force microscopy, the capture phase, for example, at least one of the monoclonal antibodies of the invention, is adhered to a solid phase and a scanning probe microscope is utilized to detect antigen/antibody complexes which may be present on the surface of the solid phase. The use of scanning tunneling microscopy eliminates the need for labels which normally must be utilized in many immunoassay systems to detect antigen/antibody complexes. The use of SPM to monitor specific binding reactions can occur in many ways. In one embodiment, one member of a specific binding partner (analyte specific substance which is the monoclonal antibody of the invention) is attached to a surface suitable for scanning. The attachment of the analyte specific substance may be by adsorption to a test piece which comprises a solid phase of a plastic or metal surface, following methods known to those of ordinary skill in the art. Or, covalent attachment of a specific binding partner (analyte specific substance) to a test piece which test piece comprises a solid phase of derivatized plastic, metal, silicon, or glass may be utilized. Covalent attachment methods are known to those skilled in the art and include a variety of means to irreversibly link specific binding partners to the test piece. If the test piece is silicon or glass, the surface must be activated prior to attaching the specific binding partner. Also, polyelectrolyte interactions may be used to immobilize a specific binding partner on a surface of a test piece by using techniques and chemistries. The preferred method of attachment is by covalent means. Following attachment of a specific binding member, the surface may be further treated with materials such as serum, proteins, or other blocking agents to minimize non-specific binding. The surface also may be scanned either at the site of manufacture or point of use to verify its suitability for assay purposes. The scanning process is not anticipated to alter the specific binding properties of the test piece.

While the present invention discloses the preference for the use of solid phases, it is contemplated that the reagents such as antibodies, proteins and peptides of the present invention can be utilized in non-solid phase assay systems. These assay systems are known to those skilled in the art, and are considered to be within the scope of the present invention.

It is contemplated that the reagent employed for the assay can be provided in the form of a test kit with one or more containers such as vials or bottles, with each container containing a separate reagent such as a probe, primer, monoclonal antibody or a cocktail of monoclonal antibodies, or a polypeptide (e.g. recombinantly, synthetically produced or purified) employed in the assay. The polypeptide is selected from the group consisting of EU250 (SEQUENCE ID NO:3), BU101 (SEQUENCE ID NO:2), TU104 (SEQUENCE ID NO:10), α' polypeptide, β' polypeptide, γ' polypeptide, and fragments thereof. Other components such as buffers, controls and the like, known to those of ordinary skill in art, may be included in such test kits. It also is contemplated to provide test kits which have means for collecting test samples comprising accessible body fluids or waste products, e.g., blood, urine, saliva and stool. Such tools useful for collection ("collection materials") include lancets and absorbent paper or cloth for collecting and stabilizing blood; swabs for collecting and stabilizing saliva; cups for collecting and stabilizing urine or stool samples. Collection materials, papers, cloths, swabs, cups and the like, may optionally be treated to avoid denaturation or irreversible adsorption of the sample. The collection materials also may be treated with or contain preservatives, stabilizers or antimicrobial agents to help maintain the integrity of the specimens. Test kits designed for the collection, stabilization and preservation of test specimens obtained by surgery or needle biopsy are also useful. It is contemplated that all kits may be configured in two components which can be provided separately; one component for collection and transport of the specimen and the other component for the analysis of the specimen. The collection component, for example, can be provided to the open market user while the components for analysis can be provided to others such as laboratory personnel for determination of the presence, absence or amount of analyte. Further, kits for the collection, stabilization and preservation of test specimens may be configured for use by untrained personnel and may be available in the open market for use at home with subsequent transportation to a laboratory for analysis of the test sample.

In Vivo Antibody Use.

Antibodies of the present invention can be used in vivo; that is, they can be injected into patients suspected of having or having diseases of the reproductive system (e.g., uterine cancer) or reproductive tissue for diagnostic or therapeutic uses. The use of antibodies for in vivo diagnosis is well known in the art. Sumerdon et al., Nucl. Med. Biol 17: 247–254 (1990) have described an optimized antibody-chelator for the radioimmunoscintographic imaging of carcinoembryonic antigen (CEA) expressing tumors using Indium-111 as the label. Griffin et al., J Clin One 9: 631–640 (1991) have described the use of this agent in detecting tumors in patients suspected of having recurrent colorectal cancer. The use of similar agents with paramagnetic ions as labels for magnetic resonance imaging is know in the art (R. B. Lauffer, Magnetic Resonance in Medicine 22: 339–342 (1991). It is anticipated that antibodies directed against the multimeric polypeptide antigen can be injected into patients suspected of having a disease of the reproductive tissue such as uterine cancer for the purpose of diagnosing or staging the disease status of the patient. The label used will depend on the imaging modality chosen. Radioactive labels such as Indium-111, Technetium-99m, or Iodine-131 can be used for planar scans or single photon emission computed tomography (SPECT). Positron emitting labels such as Fluorine-19 can also be used for positron emission tomography (PET). For MRI, paramagnetic ions such as Gadolinium (III) or Manganese (II) can be used. Localization of the label within the breast or external to the breast may allow determination of spread of the disease. The amount of label within the uterus, for example, may allow determination of the presence or absence of cancer of the uterus.

For patients known to have a disease of the reproductive tissue (e.g., uterus), injection of an antibody directed against the multimeric polypeptide antigen may have therapeutic benefit. The antibody may exert its effect without the use of attached agents by binding to the multimeric polypeptide antigen expressed on or in the tissue or organ. Alternatively, the antibody may be conjugated to cytotoxic agents such as drugs, toxins, or radionuclides to enhance its therapeutic effect. Garnett and Baldwin, Cancer Research 46: 2407–2412 (1986) have described the preparation of a drug-monoclonal antibody conjugate. Pastan et al., Cell 47: 641–648 (1986) have reviewed the use of toxins conjugated to monoclonal antibodies for the therapy of various cancers. Goodwin and Meares, Cancer Supplement 80: 2675–2680 (1997) have described the use of Yittrium-90 labeled monoclonal antibodies in various strategies to maximize the dose to tumor while limiting normal tissue toxicity. Other known cytotoxic radionuclides include Copper-67, Iodine-131, and Rhenium-186 all of which can be used to label monoclonal antibodies directed against the multimeric polypeptide antigen for the treatment of cancer of the reproductive tissue, for example, the uterus.

The present invention will now be described by way of examples, which are meant to illustrate, but not to limit, the scope of the present invention.

EXAMPLES

Example 1

Identification of Uterine Tissue Library EU250 and TU104 Gene-Specific Clones

Library Comparison of Expressed Sequence Tags (EST's) or Transcript Images. Partial sequences of cDNA clone inserts, so-called "expressed sequence tags" (EST's), were derived from cDNA libraries made from numerous tissues, both tumor and non-tumor and entered into a database (LIFESEQ™ database, available from Incyte Pharmaceuticals, Palo Alto, Calif.) as gene transcript images. See International Publication No. WO 95/20681. (A transcript image is a listing of the number of EST's for each of the represented genes in a given tissue library. EST's sharing regions of mutual sequence overlap are classified into clusters. A cluster is assigned a clone number from a representative 5' EST. Often, a cluster of interest can be extended by comparing its consensus sequence with sequences of other EST's which did not meet the criteria for automated clustering. The alignment of all available clusters and single EST's represent a contig from which a consensus sequence is derived.)

The consensus sequence of BU101 (see also published PCT application WO 97/34997) was used to query the LifeSeq EST database for homologous sequences. Incorporated, by reference, are U.S. patent application Ser. No. 08/697,105 filed on Aug. 19, 1996 which was abandoned in favor of continuation-in-part U.S. patent application Ser. No. 08/912,276 filed on Aug. 15, 1997. The latter shows a set of contiguous and partially overlapping cDNA sequences and polypeptides encoded thereby, designated as BU101 and transcribed from breast tissue which are useful for the detecting, diagnosing, staging, monitoring, prognosticating, preventing or treating, or determining the predisposition of an individual to diseases and conditions of the breast such as breast cancer.

The consensus sequence of Mam was also used to query the LifeSeq EST database for homologous sequences. Incorporated, by reference, are U.S. patent application Ser. No. 08/697,106 filed on Aug. 19, 1996 which was abandoned in favor of continuation-in-part U.S. patent application Ser. No. 08/912,149 filed on Aug. 15, 1997. The latter shows a set of contiguous and partially overlapping cDNA sequences and polypeptides encoded thereby, designated as Mam and transcribed from breast tissue which are useful for the detecting, diagnosing, staging, monitoring, prognosticating, preventing or treating, or determining the predisposition of an individual to diseases and conditions of the breast such as breast cancer.

The transcript images of the homologous sequences then were evaluated to identify EST sequences that were representative primarily of the reproductive tissue libraries.

EST's corresponding to the consensus sequence of EU250 (SEQUENCE ID NO:4) (see also published PCT application WO 97/34997) were found in 9 out of 34, or 26.5% of uterus tissue libraries. EST's corresponding to SEQUENCE ID NO:4 or fragments thereof were found in only 11 out of 1008 or 1.1% of the other, non-uterus libraries of the database. Therefore, the EST's corresponding to SEQUENCE ID NO:4, or fragments thereof were found more than 20 times more often in uterus than non-uterus tissues.

EST's corresponding to the consensus sequence of TU104 (SEQUENCE ID NO:5) (see also published PCT application WO 97/34997) were found in 4 out of 34, or 11.8% of uterus tissue libraries. EST's corresponding to SEQUENCE ID NO:5, or fragments thereof were found in only 2 out of 1008 or 0.2% of the other, non-uterus libraries of the database. Therefore, the EST's corresponding to SEQUENCE ID NO:5, or fragments thereof were found more than 50 times more often in uterus than non-uterus tissues.

In addition to those noted, three other homologous sequences were identified, but these showed specificity primarily to lung tissue libraries. Of these, one has been previously identified as the Clara Cell 10 kD Secretory Protein. The other two are LU103 (see U.S. Pat. No. 5,939,265) and LU105 (described in U.S. patent application Ser. No. 09/016,387, which was a continuation-in-part of U.S. patent application Ser. No. 08/791,710).

Example 2

Tissue Profiling of BU101, EU250, and TU104 ESTs

After identifying the homologues to BU101 and Mammaglobin, the expression of each was compared across the various tissues, divided into breast, uterus, prostate, and respiratory tissue libraries. Cytoplasmic beta actin, a "housekeeping gene" without tissue specificity, was included for comparison. The library distribution of each is shown in Table 1 below.

TABLE 1

Tissue profile of the human uteroglobin homologues.

| Tissue | Total Libs | Mamm | BU101 | EU250 | TU104 | LU105 | Clara | LU103 | beta actin |
|---|---|---|---|---|---|---|---|---|---|
| breast | 59 | 27 | 12 | 1 | 0 | 7 | 0 | 0 | 47 |
| uterus | 34 | 1 | 6 | 9 | 4 | 0 | 0 | 0 | 32 |
| prostate | 68 | 0 | 2 | 2 | 0 | 6 | 8 | 0 | 52 |
| respiratory | 73 | 0 | 0 | 1 | 0 | 25 | 29 | 31 | 60 |
| other | 808 | 2 | 5 | 7 | 2 | 6 | 7 | 6 | 628 |

From this it was seen that, while Mammaglobin was most specific to breast tissue, and EU250 and TU104 were most specific to uterus tissue, BU101 showed significant representation in both. BU101 and EU250 were also found, albeit to a lesser extent, in prostate tissue. Of the lung-specific homologues, LU103 was the most specific, occuring only in respiratory tissue libraries. Clara Cell 10 kD secretory protein occured in respiratory tissues, but also in prostate, while LU105 was present in respiratory, prostate and breast tissues.

Example 3

Phylogenetic Analysis of Uteroglobin Sequences

Known, public databases were also searched for sequences homologous to BU101 and Mam. The databases included the non-redundant protein (nrp) database, the Swissprot (SP) database (Release 38), the Swissprot-Translated European Mol Biol Lab (SP TREMBL) database (Release 11), and the Derwent database. Queries were made for both the BU101 and the Mam protein sequences. The query and retrieved sequences underwent alignment using the algorithm, PileUp, available from the Wisconsin Sequence Analysis Package (Genetics Computer Group, Madison Wis.). From this alignment, sequences that were identical but had been given different names (from the different databases) were identified and reduced to a single entry for phylogenetic analysis. Overall, fifteen unique sequences were identified and analysed for their homology based on the protein sequence. The results of the sequence alignment of these fifteen unique sequences are shown in FIG. 1.

After sequence alignment had been performed on the group of sequences, the alignment was subjected to the Distances algorithm of the Wisconsin Sequence Analysis Package (Genetics Computer Group, Madison, Wis.). The amino acids external to the first and last Cysteine residues were excluded in the analysis due to the high number of gaps present. Evolutionary analysis is best performed on the most conserved segment of sequence. The distance matrix produced is shown in Table 2 below.

6 Lipophilin A
7 Rat Prostatein, C1
8 Rat Prostatein, C2
9 Cat Major Allergen, 1a
10 Cat Major Allergen, 1b
11 Clara Cell 10 kD protein, mouse
12 Clara Cell 10 kD protein, rat
13 Uteroglobin, hare
14 Uteroglobin, rabbit
15 Clara Cell 10 kD protein, human Using these distance measurements, the algorithm produced a Growtree Phylogram as shown in FIG. 2. The phylogram is a representation of a possible route of evolution for the Uteroglobin family of proteins. Each branch point represents a point of divergence from the preceeding sequence to a newer, more evolved sequence. The measure of distance is roughly estimated from the homology between sequences. The phylogram shows clusters of sequences, including the Mammaglobin-like sequences (Mammaglobin, EU250, and Rat Prostatein C3 chain), the Clara Cell 10 kD-like sequences (Hare and Rabbit Uteroglobins and Human, Rat, and Mouse Clara Cell 10 kD proteins), the Cat Major Allergens (1α and 1β), and the BU101-like sequences (BU101, TU104, Lipophilin A, and Rat Prostatein C1 and C2 chains). The conservation of sequence over time indicates conservation of structure and function. Thus, when two sequences are known to share a high degree of homology, their structural and functional properties will be similar. Empirical knowledge of one member of a cluster can be used to predict properties about other members of the cluster. For example, the present inventors have demonstrated previously the ability of a member of the Mammaglobin cluster (Mam) to form a protein complex with a member of the BU101 cluster (BU 101) (see U.S. patent application Ser. No. 09/467,602 filed on Dec. 20, 1999 which is a continuation-in-part of U.S. patent application Ser. No. 09/215,818 filed on Dec. 18, 1998, which is a continuation-in-part of 1) U.S. patent application Ser. No. 08/912,276 filed on Aug. 17, 1997, which is a continuation-in-part of U.S. patent application Ser. No. 08/697,105 filed on Aug. 19, 1996 as well as 2) a

TABLE 2

Distance Matrix of 15 Unique Uteroglobin Sequences

| | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| 1 | | 47.83 | 57.97 | 79.69 | 82.81 | 78.12 | 78.12 | 79.69 | 76.12 | 76.12 | 72.73 | 72.73 | 72.73 | 74.24 | 75.76 |
| 2 | | | 65.22 | 79.69 | 87.50 | 82.81 | 78.12 | 75.00 | 82.09 | 82.09 | 81.82 | 81.82 | 78.79 | 80.30 | 84.85 |
| 3 | | | | 89.06 | 85.94 | 85.94 | 84.38 | 85.94 | 80.60 | 80.60 | 78.79 | 78.79 | 74.24 | 74.24 | 75.76 |
| 4 | | | | | 46.15 | 46.15 | 53.85 | 58.46 | 75.38 | 75.38 | 71.88 | 73.44 | 78.12 | 78.12 | 82.81 |
| 5 | | | | | | 55.38 | 58.46 | 66.15 | 72.31 | 72.31 | 79.69 | 79.69 | 76.56 | 76.56 | 78.12 |
| 6 | | | | | | | 63.08 | 61.54 | 72.31 | 72.31 | 76.56 | 75.00 | 73.44 | 73.44 | 75.00 |
| 7 | | | | | | | | 47.69 | 72.31 | 72.31 | 76.56 | 78.12 | 81.25 | 82.81 | 81.25 |
| 8 | | | | | | | | | 76.92 | 76.92 | 81.25 | 79.69 | 81.25 | 81.25 | 78.12 |
| 9 | | | | | | | | | | 0.00 | 73.13 | 73.13 | 74.63 | 74.63 | 73.13 |
| 10 | | | | | | | | | | | 73.13 | 73.13 | 74.63 | 74.63 | 73.13 |
| 11 | | | | | | | | | | | | 10.45 | 43.28 | 44.78 | 46.27 |
| 12 | | | | | | | | | | | | | 40.30 | 43.28 | 44.78 |
| 13 | | | | | | | | | | | | | | 7.46 | 40.30 |
| 14 | | | | | | | | | | | | | | | 43.28 |
| 15 | | | | | | | | | | | | | | | |

Seq # Name
1 Mammaglobin
2 EU250
3 Rat Prostatein, C3
4 BU101
5 TU104 continuation-in-part of U.S. patent application Ser. No. 08/912,149 filed on Sep. 15, 1997, which is a continuation-in-part of U.S. patent application Ser. No. 08/697,106 filed on Aug. 19, 1996, all of which enjoy common ownership with the present application and are incorporated in their entirety by reference). A second example involves another member of the Mammaglobin cluster (Rat Prostatein C3 chain) binding to two members of the BU101 cluster (Rat Prostatein C1 and C2 chains). The existence of another protein complex is proposed involving a member of the Mammaglobin cluster (EU250) and one or two members of the BU101 cluster (BU101 and/or TU104).

Expression of the prior examples of these complexes has been shown to be tissue specific. Man-BU has been shown to be expressed in breast tissue and Rat Prostatein complex has been shown to be expressed in prostate tissue. Data from Example 2 demonstrates that the subunits comprising the proposed new Uteroglobin complex involving EU250, BU101, and TU104 is uterine specific. By extension, the complex itself should be specific to uterus tissue. That is, while BU101 in breast tissue would occur only in complex with Mammaglobin, in uterine tissue it would occur only in complex with EU250 and/or TU104.

Example 4

Production of Antibodies Against the Multimeric Polypeptide Complex

A. Production of Polyclonal Antisera.

1. Animal Immunization using Multimeric Polypeptide Complex as Immunogen. Female white New Zealand rabbits weighing 2 kg or more are used for raising polyclonal antiserum. One week prior to the first immunization, 5 to 10 ml of blood is obtained from the animal to serve as a non-immune prebleed sample.

Purified recombinant multimeric polypeptide complex (produced in accordance with Example 9) is used to prepare the primary immunogen by emulsifying 0.5 ml of the protein complex at a concentration of 2 mg/ml in PBS (pH 7.2) which contains 0.5 ml of complete Freund's adjuvant (CFA) (Difco, Detroit, Mich.). The immunogen is injected into several sites of the animal via subcutaneous, intraperitoneal, and/or intramuscular routes of administration. Four weeks following the primary immunization, a booster immunization is administered. The immunogen used for the booster immunization dose is prepared by emulsifying 0.5 ml of the same multimeric polypeptide complex used for the primary immunogen, except that the polypeptide now is diluted to 1 mg/ml with 0.5 ml of incomplete Freund's adjuvant (IFA) (Difco, Detroit, Mich.). Again, the booster dose is administered into several sites and can utilize subcutaneous, intraperitoneal and intramuscular types of injections. The animal is bled (5 ml) two weeks after the booster immunization and the serum is tested for immunoreactivity to the multimeric polypeptide complex, as described below. The booster and bleed schedule is repeated at 4 week intervals until an adequate titer is obtained. The titer or concentration of antiserum is determined by microtiter EIA as described in Example 5. An antibody titer of 1:500 or greater is considered an adequate titer for further use and study.

2. Animal Immunization using Peptide as Immunogen. Incorporated, by reference, are U.S. patent application Ser. No. 08/697,105 filed on Aug. 19, 1996 which was abandoned in favor of U.S. patent application Ser. No. 08/912, 276 filed on Aug. 15, 1997, which describes the production of antibodies against the individual polypeptide chains, including BU101, of this multimeric polypeptide complex.

B. Production of Monoclonal Antibody.

1. Immunization Protocol Using Multimeric Polypeptide Complex as Immunogen. Mice are immunized using immunogens prepared as described in Example 9, except that the amount of the multimeric polypeptide complex for monoclonal antibody production in mice is one-tenth the amount used to produce polyclonal antisera in rabbits. Thus, the primary immunogen consists of 100 µg of the multimeric polypeptide complex in 0.1 ml of CFA emulsion; while the immunogen used for booster immunizations consists of 50 µg of the multimeric polypeptide complex in 0.1 ml of IFA. Hybridomas for the generation of monoclonal antibodies are prepared and screened using standard techniques. The methods used for monoclonal antibody development follow procedures known in the art such as those detailed in Kohler and Milstein, Nature 256: 494 (1975) and reviewed in J. G. R. Hurrel, ed., Monoclonal Hybridoma Antibodies: Techniques and Applications, CRC Press, Inc., Boca Raton, Fla. (1982). Another method of monoclonal antibody development which is based on the Kohler and Milstein method is that of L. T. Mimms et al., Virology 176: 604–619 (1990), which is incorporated herein by reference.

The immunization regimen (per mouse) consists of a primary immunization with additional booster immunizations. The primary immunogen used for the primary immunization consists of 100 µg of the multimeric polypeptide complex in 50 µl of PBS (pH 7.2) previously emulsified in 50 µl of CFA. Booster immunizations performed at approximately two weeks and four weeks post primary immunization consist of 50 µg of the multimeric polypeptide complex in 50 µl of PBS (pH 7.2) emulsified with 50 µl IFA. A total of 100 µl of this immunogen is inoculated intraperitoneally and subcutaneously into each mouse. Individual mice are screened for immune response by microtiter plate enzyme immunoassay (EIA) as described in Example 5 approximately four weeks after the third immunization. Mice are inoculated either intravenously, intrasplenically or intraperitoneally with 50 µg of the multimeric polypeptide complex in PBS (pH 7.2) approximately fifteen weeks after the third immunization.

Three days after this intravenous boost, splenocytes are fused with, for example, Sp2/0-Ag14 myeloma cells (Milstein Laboratories, England) using the polyethylene glycol (PEG) method. The fusions are cultured in Dulbecco's Modified Eagle's Medium (DMEM) with the addition of L-glutamine, L-asparagine, L-arginine, folic acid, and containing 10% fetal calf serum (FCS), plus 1% hypoxanthine, aminopterin and thymidine (HAT). Bulk cultures are screened by microtiter plate EIA following the protocol in Example 5. Clones reactive with the multimeric polypeptide complex used as immunogen and non-reactive with other unrelated proteins are selected for final expansion. Clones thus selected are expanded, aliquoted and frozen in DMEM containing 10% FCS and 10% dimethyl sulfoxide.

2. Immunization Protocol Using Peptide as Immunogen. Mice were immunized using peptide/carrier immunogens (peptides conjugated to a carrier protein) prepared as described previously in U.S. patent application Ser. No. 08/697, 105 filed on Aug. 19, 1996 which was abandoned in favor of U.S. patent application Ser. No. 08/912, 276 filed on Aug. 15, 1997. The amount of the peptide/carrier protein immunogen used for monoclonal antibody production in mice was approximately one-tenth the amount used to produce polyclonal antisera in rabbits. Thus, the primary immunogen consisted of 100 µg of the peptide conjugated to a carrier protein in 0.1 ml of CFA emulsion; while the immunogen used for booster immunizations consisted of 50 µg the peptide/carrier protein in 0.1 ml of IFA. Hybridomas for the generation of monoclonal antibodies were prepared and screened using standard techniques. The methods used for monoclonal antibody development followed procedures known in the art such as those detailed in Kohler and Milstein, Nature 256: 494 (1975) and reviewed in J. G. R. Hurrel, ed., Monoclonal Hybridoma Antibodies: Techniques and Applications, CRC Press, Inc., Boca Raton, Fla. (1982). Another method of monoclonal antibody development which is based on the Kohler and Milstein method is that of L. T. Mimms et al., Virology 176: 604–619 (1990), which is incorporated herein by reference.

The immunization regimen (per mouse) consisted of a primary immunization with additional booster immunizations. The primary immunogen used for the primary immunization consisted of 100 μg of the peptide/carrier protein complex in 50 μl of PBS (pH 7.2) previously emulsified in 50 μl of CFA. Booster immunizations performed at approximately two weeks and four weeks post primary immunization consisted of 50 μg of the peptide/carrier protein complex in 50 μl of PBS (pH 7.2) emulsified with 50 μl IFA. A total of 100 μl of this immunogen was inoculated intraperitoneally into each mouse. Individual mice were screened for immune response by microtiter plate enzyme immunoassay (EIA) as described in Example 5 approximately four weeks after the third immunization. Mice were inoculated intravenously with 25 μg of the peptide/carrier protein complex in PBS (pH 7.2) approximately fifteen weeks after the third immunization.

Three days after this intravenous boost, splenocytes were fused with Sp2/0-Ag14 myeloma cells (Milstein Laboratories, England) using the polyethylene glycol (PEG) method. The fusions were cultured in Dulbecco's Modified Eagle's Medium (DMEM) with the addition of L-glutamine, L-asparagine, L-arginine, folic acid, and containing 10% fetal calf serum (FCS), plus 1% hypoxanthine, aminopterin and thymidine (HAT). Bulk cultures were screened by microtiter plate EIA following the protocol in Example 5. Clones reactive with the multimeric polypeptide complex and the peptide used as immunogen and non-reactive with other unrelated proteins were selected for final expansion. Supernatant from the final expansion was harvested and used for further characterisation. The hybridoma cells from the expansion growth were harvested, aliquoted, and frozen in DMEM containing 10% FCS and 10% dimethyl sulfoxide for storage.

3. Production of Ascites Fluid Containing Monoclonal Antibodies. Frozen hybridoma cells, prepared as described hereinabove, were thawed and placed into expansion culture. Viable hybridoma cells were inoculated intraperitoneally into Pristane treated mice. Ascitic fluid was removed from the mice, pooled, filtered through a 0.2μ filter and subjected to an immunoglobulin class G (IgG) analysis to determine the volume of the Protein A column required for the purification.

4. Purification of Monoclonal Antibodies From Ascites Fluid or Cell Culture Supernatant. Monoclonal antibodies can be purified from ascites fluid or cell culture supernatant using a variety of methods including Protein A, Protein G, and Protein L column chromatography or precipitation. Monoclonal antibody H85C21 was purified using an Immunopure(G) IgG Purification kit (Pierce). Forty seven milliliters of the H85C21 culture supernatant that contained 29 ug/mL of IgG was mixed with 100 mLs of the binding buffer (0.02 M sodium phosphate, pH 7.0) (Pierce). One hundred forty five milliliters of the mixture were passed over a Protein G column that was equilibrated with the binding buffer. The column was then eluted with elution buffer (0.1 M glycine-HCl, pH 2.7) (Pierce). One milliliter fractions were collected in tubes that contained 100 uL of 1M sodium bicarbonate for neutralization. Fractions were monitored for absorbance at 280 nm. Appropriate fractions were pooled and dialyzed against PBS (pH 7.2) overnight at 2–8° C. Absorbance at 280 nm indicated that 1.51 mg of IgG was recovered from the Protein G column. The purified monoclonal antibody thus prepared and characterized was placed at −80° C. for long term storage.

5. Further Characterization of Monoclonal Antibody. The isotype and subtype of the monoclonal antibodies produced as described hereinabove was determined using an EIA microtiter plate assay. Briefly, the peptide immunogen was prepared at 1 mg/mL in 50 mM carbonate, pH 9.6 and 100 μl was placed in each well of an Immulon 2® High Binding microtiter plate (Dynex Technologies, Chantilly, Va.). The plate was incubated for 14–18 hours at room temperature and then washed four times with deionized water. The wells were blocked by adding 200 μl of Superblock® (Pierce Chemical Company, Rockford, Ill.) to each well and incubated at room temperature for 30 minutes before discarding the solution. Antisera obtained from immunized rabbits and mice, as described hereinabove, were diluted in a protein blocking agent (i.e., 3% Superblock® solution) in PBS containing 0.05% Tween-20 (monolaurate polyoxyethylene ether) (Sigma Chemical Company, St. Louis, Mo.) and 0.05% sodium azide and placed in each well of the coated microtiter plate. The wells were then incubated for one hour at room temperature. Each well was washed four times with deionized water. One hundred microliters (100 μl) of alkaline phosphatase-conjugated goat anti-mouse IgG (H+L), or IgG1, or IgG2a, or IgG2b, or IgG3 (Southern Biotech, Birmingham, Ala.), diluted 1:2000 in 3% Superblock® solution was added to each well. The wells were incubated for one hour at room temperature. Next, each well was washed four times with deionized water. One hundred microliters (100 μl) of para-nitrophenyl phosphate substrate (Kirkegaard and Perry Laboratories, Gaithersburg, Md.) then was added to each well. The wells were incubated for thirty minutes at room temperature. The absorbance at 405 mm was read in each well. The results of the isotype testing are presented in Table 3.

Stability testing also can be performed on the monoclonal antibody by placing an aliquot of the monoclonal antibody in continuous storage at 2–8° C. and assaying optical density (OD) readings throughout the course of a given period of time.

TABLE 3

Characterization of Monoclonal Antibodies

| Study # | Experiment # | Hybridoma | Peptide Immunogen | Isotype |
|---|---|---|---|---|
| 390 | 1 | H85C21 | BU101.8 | IgG1 |
| 390 | 1 | H171C113 | BU101.8 | IgG1 |
| 390 | 2 | H155C16 | BU101.8 | IgG1 |
| 394 | 4 | H1C81 | BU101.9 | IgG1 |
| 394 | 4 | H9C65 | BU101.9 | IgG1 |
| 394 | 4 | H17C51 | BU101.9 | IgG1 |
| 394 | 4 | H27C79 | BU101.9 | IgG1 |
| 394 | 4 | H50C22 | BU101.9 | IgG1 |
| 394 | 4 | H51C26 | BU101.9 | IgG1 |
| 394 | 4 | H54C62 | BU101.9 | IgG1 |
| 394 | 4 | H91C52 | BU101.9 | IgG1 |
| 394 | 4 | H92C70 | BU101.9 | IgG1 |
| 394 | 4 | H87C44 | BU101.9 | IgG1 |
| 394 | 5 | H8C70 | BU101.3 | IgG1 |
| 394 | 5 | H20C81 | BU101.3 | IgG1 |
| 394 | 5 | H65C16 | BU101.3 | IgG1 |
| 394 | 5 | H68C68 | BU101.3 | IgG1 |
| 394 | 5 | H73C40 | BU101.3 | IgG1 |

TABLE 3-continued

Characterization of Monoclonal Antibodies

| Study # | Experiment # | Hybridoma | Peptide Immunogen | Isotype |
|---|---|---|---|---|
| 394 | 5 | H80C20 | BU101.3 | IgG1 |
| 394 | 5 | H90C34 | BU101.3 | IgG1 |
| 394 | 5 | H95C30 | BU101.3 | IgG1 |
| 392 | 17 | H9C81 | BU101.8 | IgG1 |
| 392 | 17 | H34C68 | BU101.8 | IgG1 |

Example 5

Enzyme Immunoassays

A. Microtiter Plate Direct Detection EIA.

The immunoreactivity of polyclonal and/or monoclonal antiserum (against either BU101, EU250, or TU104) toward the recombinant polypeptide complex is determined by means of a microtiter plate EIA. For antibody titer measurements, pooled and dialysed recombinant polypeptide complex is prepared at 2 ug/mL in 50 mM carbonate buffer, pH 9.6 and 100 µl is placed in each well of an Immulon 2® High Binding microtiter plate (Dynex Technologies, Chantilly, Va.). The plate is incubated for 14–18 hours at room temperature and then washed four times with deionized water. The wells are blocked by adding 200 µl of Superblock® (Pierce Chemical Company, Rockford, Ill.) to each well and the plates are incubated at room temperature for 30 minutes before discarding the solution. Antisera obtained from immunized rabbits and mice, as described hereinabove in Example 4, are diluted 1:10, 1:100, 1:1000, 1:10000, 1:100000 in a protein blocking i.e., 3% Superblock® solution) in PBS containing 0.05% Tween-20 (monolaurate ethylene ether) (Sigma Chemical Company, St. Louis, Mo.) and 0.05% sodium nd placed in each well of the coated microtiter plate. The wells are then incubated for one hour at room temperature. Each well is washed four times with deionized water. One hundred microliters (100 µl) of alkaline phosphatase-conjugated goat anti-mouse IgG (Southern Biotech, Birmingham, Ala.), diluted 1:2000 in 3% Superblock® solution is added to each well. The wells are incubated for one hour at room temperature. Next, each well is washed four times with deionized water. One hundred microliters (100 µl) of para-nitrophenyl phosphate substrate (Kirkegaard and Perry Laboratories, Gaithersburg, Md.) then is added to each well. The wells are incubated for thirty minutes at room temperature. The absorbance at 405 nm is read in each well. The titer is designated as the dilution of antibody that results in an absorbance of 0.5 units at 405 nm.

In addition to titers, apparent affinities [$K_d$(app)] are also determined for some of the anti-peptide antisera. In this case, pooled and dialysed recombinant polypeptide complex is prepared at dilutions of 1:3, 1:9, 1:27, 1:81, 1:243, 1:729, 1:2187, 1:6561, and 1:19683 in PBS and 100 µl is placed in each well of an Immulon 2® High Binding microtiter plate (Dynex Technologies, Chantilly, Va.). The plate is incubated for 14–18 hours at room temperature and then washed four times with deionized water. The wells are blocked by adding 200 µl of Superblock® (Pierce Chemical Company, Rockford, Ill.) to each well and the plates are incubated at room temperature for 30 minutes before discarding the solution. Antisera obtained from immunized rabbits and mice, as described hereinabove in Example 4, are diluted at an appropriate dilution in a protein blocking agent (i.e., 3% Superblock® solution) in PBS containing 0.05% Tween-20 (monolaurate polyoxyethylene ether) (Sigma Chemical Company, St. Louis, Mo.) and 0.05% sodium azide and are placed in each well of the coated microtiter plate. The wells are then incubated for one hour at room temperature. Each well is washed four times with deionized water. One hundred microliters (100 µl) of alkaline phosphatase-conjugated goat anti-mouse IgG (Southern Biotech, Birmingham, Ala.), diluted 1:2000 in 3% Superblock® solution is added to each well. The wells are incubated for one hour at room temperature. Next, each well is washed four times with deionized water. One hundred microliters (100 µl) of para-nitrophenyl phosphate substrate (Kirkegaard and Perry Laboratories, Gaithersburg, Md.) then is added to each well. The wells are incubated for thirty minutes at room temperature. The absorbance at 405 nm is read in each well. EIA microtiter plate assay results are used to derive the apparent dissociation constants [$K_{d(app)}$] based on an analog of the Michaelis-Menten equation (V. Van Heyningen, Methods in Enzymology, Vol. 121, p. 472 (1986) and further described in X. Qiu, et al, Journal of Immunology, Vol. 156, p. 3350 (1996)):

$$[Ag - Ab] = [Ag - Ab]_{max} X \frac{[Ab]}{[Ab] + K_d}$$

where [Ag-Ab] is the antigen-antibody complex concentration, [Ag-Ab]$_{max}$ is the maximum complex concentration, [Ab] is the antibody concentration, and $K_d$ is the dissociation constant. During the curve fitting, the [Ag-Ab] is replaced with the background subtracted value of the OD$_{405\ nm}$ at the given concentration of Ab. Both $K_d$, which corresponds to Kd(app), and [OD$_{405\ nm}$]$_{max}$, which corresponds to the [Ag-Ab]$_{max}$, are treated as fitted parameters. The software program Origin is used for the curve fitting.

B. Microtiter Plate Sandwich EIA.

Briefly, samples suspected of containing the multimeric polypeptide antigen are incubated in the presence of any combination of the following anti-BU101, anti-EU250, anti-TU104, or anti-multimeric polypeptide antibody-coated microtiter wells in order to form antigen/antibody complexes. The microtiter wells then are washed and an indicator reagent comprising an antibody conjugated to a signal generating compound (i.e., enzymes such as alkaline phosphatase or horseradish peroxide) is added to the antigen/antibody complexes on the microtiter wells and incubated. The microtiter wells are washed and the bound antibody/antigen/antibody complexes are detected by adding a substrate (e.g., 4-methyl umbelliferyl phosphate (MUP), or OPD/peroxide, respectively), that reacts with the signal generating compound to generate a measurable signal. An elevated signal in the test sample, compared to the signal generated by a negative control, detects the presence of the multimeric polypeptide antigen. The presence of the multimeric polypeptide antigen in the test sample is indicative of a diagnosis of a breast disease or condition, such as breast cancer.

In an analogous manner, samples suspected of containing the multimeric polypeptide antigen are incubated in the presence of any combination of the following steroid (progesterone, aldosterone, androstenedione, corticosterone, cortisol, dehydroepiandrosterone, dihydrotestosterone, estradiol, estriol, estrone, hydroxyprogesterone, or testosterone) coated microtiter wells in order to form antigen/steroid complexes. The microtiter wells then are washed and an indicator reagent comprising either an antibody or a steroid conjugated to a signal generating compound is added to the steroid/antigen complexes on the microtiter wells and incubated. The microtiter wells are washed and the bound steroid/antigen/indicator reagent complexes are detected by adding a substrate that reacts with the signal generating compound to generate a measurable signal. An elevated signal in the test sample, compared to the signal generated by a negative control, detects the presence of the multimeric polypeptide antigen. The presence of the multimeric polypeptide antigen in the test sample is indicative of a diagnosis of a breast disease or condition, such as breast cancer.

C. Microtiter Plate Competitive EIA.

The competitive binding assay uses a labeled polypeptide or protein complex that generates a measurable signal when the labeled polypeptide or protein complex is contacted with a microtiter well coated with an anti-polypeptide antibody. The labeled polypeptide is added to the multimeric polypeptide antibody-coated microtiter well in the presence of a test sample suspected of containing the multimeric polypeptide antigen, and incubated for a time and under conditions sufficient to form labeled peptide (or labeled protein)-bound antibody complexes and/or patient antigen-bound antibody complexes. The multimeric polypeptide antigen in the test sample competes with the labeled polypeptide (or protein) for binding sites on the microtiter well. The multimeric polypeptide antigen in the test sample results in a lowered binding of labeled peptide to the antibody-coated microtiter wells in the assay since antigen in the test sample and the peptide or protein compete for antibody binding sites. A lowered signal (compared to a control) indicates the presence of the multimeric polypeptide antigen in the test sample. The presence of the multimeric polypeptide antigen suggests the diagnosis of a reproductive tissue disease or condition, such as uterine cancer.

Similarly, the competitive binding assay uses a labeled polypeptide or protein complex that generates a measurable signal when the labeled polypeptide or protein complex is contacted with a microtiter well displaying a steroid. The labeled polypeptide is added to the steroid coated microtiter well in the presence of a test sample suspected of containing the multimeric polypeptide antigen, and incubated for a time and under conditions sufficient to form labeled peptide (or labeled protein)-bound steroid complexes and/or patient antigen-bound steroid complexes. The multimeric polypeptide antigen in the test sample competes with the labeled polypeptide (or protein) for binding sites on the microtiter well. The multimeric polypeptide antigen in the test sample results in a lowered binding of labeled peptide to the steroid-coated microtiter wells in the assay since antigen in the test sample and the peptide or protein compete for steroid binding sites. A lowered signal (compared to a control) indicates the presence of the multimeric polypeptide antigen in the test sample. The presence of the multimeric polypeptide antigen suggests the diagnosis of a reproductive tissue disease or condition, such as uterine cancer.

The multimeric polypeptide complex which is provided and discussed hereinabove is useful as a marker of reproductive tissue disease, especially uteine cancer. Tests based upon the appearance of this marker in a test sample such as tissue, blood, plasma or serum can provide low cost, non-invasive, diagnostic information to aid the physician to make a diagnosis of cancer, to help select a therapy protocol, or to monitor the success of a chosen therapy. This marker may appear in readily accessible body fluids such as blood, urine or stool as antigens derived from the diseased tissue which are detectable by immunological methods. This marker may be elevated in a disease state, altered in a disease state, or be a normal protein of the uterus which appears in an inappropriate body compartment.

Example 6

Immunoprecipitation of the Multimeric Polypeptide Complex

Immune sera, obtained as described hereinabove in Example 4, is used to immunoprecipitate the multimeric polypeptide complex from solution prepared from tissue, blood, serum, or other bodily fluid. For tissue specimens, protein extracts are prepared by homogenizing tissue samples in 0.1M Tris-HCl (pH 7.5), 15% (w/v) glycerol, 0.2 mM EDTA, 10 µg/ml leupeptin and 1.0 mM phenylmethylsulfonylfluoride [Kain et al., *Biotechniques*, 17: 982 (1994)]. Following homogenization, the homogenates are centrifuged at 2000×g at 4° C. for 5 minutes to separate supernatant from debris. Debris is re-extracted by homogenization with a buffer that is similar to above but also contains 0.1M Tricine and 0.1% SDS. Serum specimens can be used directly. Other bodily fluids may require preparation before immunoprecipitation.

The immunoprecipitation begins by coupling the antigen (if present) to the antibody by placing the sample (10–200 µl) in an Eppendorf tube. Bring the volume to 200 µl with dilution buffer (10 mM tris-HCl, pH 8.0, 150 mM NaCl, 0.1% triton X-100, 0.025% sodium azide, 0.1% bovine serum albumin). Add the polyclonal serum (0.5–5 µl), hybridoma culture supernatant (10–100 µl), or ascites fluid (0.1–1 µl). Gently mix for 1.5 to 6 hours at room temperature. Precipitate the immune complex by adding 20–40 µl of 50% Protein A Sepharose slurry (Pharmacia Biotech, Piscataway, N.J.). Gently mix for 1.5 to 16 hours. Centrifuge 1 minute at 200×g. Carefully remove supernatant and save pellet. Wash pellet with 1 mL of 10 mM tris-HCl, pH 8.0, 150 mM NaCl, 0.025% sodium azide followed by 1 mL of 50 mM tris-HCl, pH 6.8. Again, carefully remove supernatant and save pellet. Dissociate the immune complex by adding 20–50 µl of SDS-PAGE buffer (50 mM tris-HCl, pH 6.8, 10% glycerol, 2% SDS, 2% beta-mercaptoethanol, 0.01% bromphenol blue) to the washed Protein A Sepharose beads. Cap and heat the sample at 100 C. for five minutes. Microfuge to pellet the Sepharose. Apply the supernatant to SDS-polyacrylamide gels and proceed with electrophoresis as described in Example 9. After SDS-PAGE, the antigen can be detected by protein staining, immunoblotting, and/or radiography.

Example 7

Purification of Serum Antibodies Which Specifically Bind to Polypeptides

Immune sera, obtained as described hereinabove in Example 4, is affinity purified using immobilized recombinant polypeptide complex prepared as in accordance with Example 9. An IgG fraction of the antiserum is obtained by passing the diluted, crude antiserum over a Protein A column (Affi-Gel protein A, Bio-Rad, Hercules, Calif.). Elution with a buffer (Binding Buffer, supplied by the manufacturer) removes substantially all proteins that are not immunoglobulins. Elution with 0.1M buffered glycine (pH 3) gives an immunoglobulin preparation that is substantially free of albumin and other serum proteins.

Immunoaffinity chromatography is performed to obtain a preparation with a higher fraction of specific antigen-binding antibody. The polypeptide used to raise the antiserum is immobilized on a chromatography resin, and the specific antibodies directed against its epitopes are adsorbed to the resin. After washing away non-binding components, the specific antibodies are eluted with 0.1 M glycine buffer, pH 2.3. Antibody fractions are immediately neutralized with 1.0 M Tris buffer (pH 8.0) to preserve immunoreactivity. The chromatography resin chosen depends on the reactive groups present in the polypeptide. If the polypeptide has an amino group, a resin such as Affi-Gel 10 or Affi-Gel 15 is used (Bio-Rad, Hercules, Calif.). If coupling through a carboxy group on the polypeptide is desired, Affi-Gel 102 can be used (Bio-Rad, Hercules, Calif.). If the polypeptide has a free sulfhydryl group, an organomercurial resin such as Affi-Gel 501 can be used (Bio-Rad, Hercules, Calif.).

Alternatively, spleens can be harvested and used in the production of hybridomas to produce monoclonal antibodies following routine methods known in the art as described hereinabove.

Example 8

Immunohistochemical Detection of the Multimeric Polypeptide Complex

Monoclonal antibodies, as described herein in Example 4, are used to immunohistochemically label a formalin-fixed paraffin-embedded cell line (as described hereinbelow in Example 9) as well as malignant and normal tissues using standard procedures. D. L. Spector et al, In: *Cells: A Laboratory Manual*, Plainview, N.Y.: Cold Spring Harbor Laboratory Press 1998. Briefly, 5 μm sections are cut and placed on positively charged slides which are heated on a slide warmer at 60 C. for 30 minutes. The sections are rehydrated twice in zylene for 5 minutes each, twice in 100% ethanol for 1 minute each, three times in 95% ethanol for 1 minute each, and distilled water for 3 minutes. The sections are heated for 30 minutes in a Black and Decker Vegetable Steamer in 10 mM citrate buffer pH 6.0 and then cooled for 20 minutes to room temperature. The sections are washed in distilled water for 5 minutes and then blocked for 15 minutes with 1× casein (Dako Corp., Carpinteria, Calif.) diluted in tris-buffered-saline [0.05 M Tris-HCl pH 7.6, 0.15 M NaCl] (TBS). The hybridoma culture supernatant is diluted 1:1 in TBS. This diluted supernatant is added to the sections and incubated at room temperature for 60 minutes, then is washed twice in TBS for 5 minutes each. For detection, the LSAB+ kit (Dako Corp., Carpinteria, Calif.) is used. The sections are incubated with the link antibody for 30 minutes at room temperature and then are washed twice in TBS for 5 minutes each. The sections then are incubated with streptavidin for 30 minutes at room temperature and washed twice in TBS for 5 minutes each. The sections are developed with BCIP/NBT/INT substrate (Dako Corp., Carpinteria, Calif.) for 15 minutes, placed in distilled water, and mounted with aqueous mounting media. The sections are viewed with a Nikon Optiphot II light microscope with a 10× objective and recorded with a Photometrics CoolSnap CCD camera and Metamorph version 4.0 software.

Example 9

Stable Transfection and Expression of a Complex Comprising EU250 M/H, TU104 M/H, and BU101 M/H from Human Embryonic Kidney 293 Cells A. Production of Stable Cell Line.

Incorporated, by reference, is U.S. patent application Ser. No. 08/697,105 filed on Aug. 19, 1996, which was abandoned in favor of U.S. patent application Ser. No. 08/912,276 filed on Aug. 15, 1997, which describes the production of BU101 myc/his (M/H) expression plasmids which utilized either clone 603148 or clone 2083578. Expression plasmids for TU104 M/H and EU250 M/H are prepared in an anologous manner. These expression plasmids are retransformed into DH5 alpha cells, plated onto LB/ampicillin agar, and grown up in 10 ml of LB/ampicillin broth. The plasmids are purified using a QIAfilter™ Maxi Kit (Qiagen, Chatsworth, Calif.) and are transfected into HEK293 cells [F. L. Graham et al., *J. Gen. Vir.* 36: 59–72 (1977)].

The purified expression plasmids, as described supra, are transfected into HEK293 cells [F. L. Graham et al., *J. Gen. Vir.* 36: 59–72 (1977)]. These cells are available from the A.T.C.C., 10801 University Boulevard. Manassas, Va. 20110, under Accession No. CRL, 1573. Transfection of the EU250 M/H, TU104 M/H, and BU101 M/H expression plasmids is performed using the cationic lipofectamine-mediated procedure described by P. Hawley-Nelson et al., Focus 15.73 (1993). Particularly, HEK293 cells are cultured in 10 ml DMEM media supplemented with 10% fetal bovine serum (FBS), L-glutamine (2 mM), sodium pyruvate (1 mM) and essential amino acids and freshly seeded into 60 mm culture plates at a density of $9 \times 10^6$ cells per plate. The cells are grown at 37° C. to a confluency of between 70% and 80% for transfection. Two micrograms of EU250 M/H plasmid DNA, two micrograms of TU104 M/H plasmid DNA, and two micrograms of BU101 M/H plasmid DNA are added to 800 μl of unsupplemented DMEM medium (Gibco-BRL, Grand Island, N.Y.). 8 ul of Plus Reagent (Gibco-BRL, Grand Island, N.Y.) is added to this solution, which is then mixed briefly. 12 ul of Lipofectamine (LTI) is added to a second 800 μl portion of unsupplemented DMEM media. After a fifteen minute incubation, the two solutions are mixed and incubated at room temperature for an additional 15–30 minutes. During this time the culture medium is removed from the plates containing the HEK293 cells. The DMEM containing the Plus reagent:Lipofectamine::plasmid DNA complex is then overlaid onto the cells. The cells are incubated for 5 hr at 37° C. and 5% $CO_2$, after which time, an additional 2–8 mL of DMEM with 20% FBS are added. After 18–24 hr, the old medium is aspirated, and the cells are overlaid with 5 mL of fresh DMEM with 5% FBS containing 400 ug/ml G418, and the incubation is continued until 72 hrs has elapsed. Supernatants are analyzed for EU250 M/H, TU104 M/H, and BU101 M/H polypeptide expression by Western blot analysis.

At 72 hours post transfection, the cells are released from the dish by limited trysinization and are reseeded into 100 mm culture dishes in DMEM, 10% FBS, 400 ug/ml G418 at dilutions of 1:100, 1:1000 and 1:10000. These cultures are allowed to grow for 5–7 days, until well-isolated foci of cells are identified by microscopy. These foci are isolated by cloning cylinders, their cells released by limited trypsinization, and individual foci are transferred to separate wells in 24-well dishes, again in DMEM, 10% FBS, 400 ug/ml G418. After growth for 7–10 days, the supernatants of each well are analysed for EU250 M/H, TU104 M/H, and BU101 M/H expression by Western blot analysis, as described hereinbelow. The final product of this procedure is a cell line derived from HEK293 cell line that expresses EU250 M/H, TU104 M/H, and BU101M/H.

B. Analysis of Media

Aliquots of the supernatants from the stable cell line are analyzed for the presence of EU250 M/H, TU104 M/H, and BU101 M/H recombinant proteins. The aliquots are prepared in a reducing sample buffer (final concentration of 50 mM tris pH 6.8, 10% glycerol (v/v), 2% sodium dodecyl sulfate (w/v), 2% beta-mercaptoethanol (v/v), 0.01% bromphenol blue (w/v)) and are then electrophoresed on SDS-polyacrylamide gels (SDS-PAGE) using standard methods and reagents known in the art. (J. Sambrook et al., supra) Specifically, 40 µl of sample is added to 10 µl of sample buffer (5×) and the mixture is boiled for 5–10 minutes. Fifteen µl of that prepared sample is then loaded on a 10–20% Tricine gel, 1 mm thick, (Novex, San Diego, Calif.) and electrophoresed at 110 V for approximately 90 minutes. These gels are then blotted overnight at 20V onto a solid medium such as nitrocellulose. The EU250 M/H, TU104 M/H, and BU101 M/H protein bands are visualized using Western blotting techniques with a monoclonal antibody recognizing a myc epitope (Invitrogen, Carlsbad, Calif.) or polyclonal antisera recognizing EU250, TU104, or BU101. Specifically, the nitrocellulose blot is removed and blocked with 0.2% I-block® (Tropix, Bedford, Mass.) for 60 minutes at room temperature. An appropriate amount of the primary antibody is then added. For example, the polyclonal antisera are used at a dilution of 1:5000 and the anti-myc epitope monoclonal antibody is used at a dilution of 1:5000. The primary antibody solution is exposed to the blot for 60 minutes at room temperature with shaking. The blot is then washed three times with I-block® solution. The secondary antibody, including either biotinylated goat anti-rabbit IgG or biotinylated goat anti-mouse IgG, is then prepared in I-block® solution at an appropriate dilution (1:5000) and exposed to the blot for 60 minutes at room temperature with shaking. The blot is then washed three times with I-block® solution. The conjugate, alkaline phosphatase labeled streptavidin, is then prepared in I-block® solution at an appropriate dilution (1:10,000) and exposed to the blot for 30 minutes at room temperature with shaking. The blot is then washed three times with I-block® solution, followed by two times with assay buffer (20 mM tris (pH 9.8)/1 mM magnesium chloride). Twenty five milligrams of 5-bromo-4-chloro-3-indolyl phosphate, BCIP, is dissolved in 0.5 mL of dimethylformamide. One hundred microliters of this BCIP solution is then mixed with 30 mLs of assay buffer and this BCIP substrate solution is exposed to the blot until bands are visible. The blot is then removed from the substrate solution and allowed to dry in the air. Electronic copies of the blots are obtained by scanning the dried blot.

C. Nickel Chelation Chromatography

Supernatant from the growth of the stable cell line, as described supra, is applied to Chelating Sepharose Fast Flow (Pharmacia) charged with nickel for the purification of is M/H tagged proteins. Specifically, 40 mLs of Chelating Sepharose Fast Flow is packed into a 16 mm×10 cm column. Forty milliliters of nickel sulfate (0.1 M) in water are passed over the column to charge it with nickel. The column is washed and equilibrated with 10 mM sodium phosphate, 500 mM sodium chloride, pH 7.4. Supernatant from the growth of the stable cell line is applied to the equilibrated column, and the histidine tagged proteins are eluted using a linear gradient of imidazole. One hundred microliters of each fraction is applied to a well of a dot blot apparatus and the volume is suctioned through a piece of nitrocellulose. The nitrocellulose filter is then developed with the same procedure to develop Western blots, as described hereinabove in Example 9, using a monoclonal antibody recognizing a myc epitope. Positive fractions are pooled and dialysed for a minimum of 4 hours each, against 2×4 L of phosphate buffered saline (PBS, 50 mM phosphate, 150 mM sodium chloride, pH 7.4) using Slide-a-Lysers (3500 MWCO). The pooled, dialysed, semi-purified supernatant is analysed for the presence of EU250 M/H, TU104 M/H, and BU101 M/H recombinant proteins by Western blot.

D. Isoelectric Focusing

The isoelectric point of the proteins of interest is determined using the isoelectric function of the Wisconsin Sequence Analysis Package (Genetics Computer Group). The isoelectric point is a property of all proteins and is the pH at which the protein has zero net charge. Thomas E. Creighton, ed., Proteins; Structures and Molecular Properties, $2^{nd}$ edition, W H Freeman and Company, NY (1993). Table 4 lists the pI of the proteins of interest.

TABLE 4

Isoelectric Points of the Proteins of Interest

| Protein | PI no M/H tag |
|---|---|
| EU250 | 5.6 |
| BU101 | 8.4 |
| TU104 | 8.5 |

The pooled, dialysed, semi-purified supernatant (from nickel chelation chromatography) is prepared for isoelectric focusing using IEF 3–10 gels, cathode buffer pH 3–10, anode buffer, and sample buffer pH 3–10 (Novex) according to the manufacturer's instructions. Briefly, 50 uL of supernatant is added to 50 uL of sample buffer. Thirty microliters are loaded into each well of the gel. The gel is electrophoresed at 100 V for one hour, then 200 V for one hour, and finally 500 V for half an hour. The gel is blotted onto nitrocellulose overnight at 22 V constant voltage. The Western blot is developed as described hereinabove in Example 9 with anti-myc monoclonal antibody.

E. Ion Exchange Chromatography

Semi-purified supernatant from the growth of the stable cell line, after nickel chelation chromatography, is further purified using anion exchange chromatography. Nickel purified supernatant, as described hereinabove in Example 9, is dialysed against 2 L of 20 mM piperazine, pH 6.0. This material is applied to a Mono Q 5/5 column (Pharmacia) equilibrated with 20 mM piperazine, pH 6.0. The proteins are eluted using a linear gradient of sodium chloride. Each fraction is sampled. One hundred microliters of each fraction is boiled in the presence of 0.1% beta-mercaptoethanol, cooled, and is then applied to a well of a dot blot apparatus and the volume is suctioned through a piece of nitrocellulose. The nitrocellulose filter is then developed with the same procedure to develop Western blots, as described herein in Example 9, using a monoclonal antibody recognizing a myc epitope.

F. Gel Filtration Chromatography

Semi-purified supernatant from the growth of the stable cell line, after nickel chelation chromatography, is further purified using gel filtration chromatography. Specifically, supernatant, as described supra, is applied to a 10 mm×30 cm column of Superose 12 (Pharmacia). The column is run with a single buffer of PBS (50 mM phosphate, 150 mM sodium chloride, pH 7.4) at a flowrate of 0.4 mL/min. The column is calibrated with molecular weight standards available from Pharmacia.

The elution of the myc-his tagged EU250, TU104, and BU101 proteins from the Superose 12 column is monitored by immunorecognition with anti-myc monoclonal antibody. Each fraction is sampled. One hundred microliters of each fraction is boiled in the presence of 0.1% beta-mercaptoethanol, cooled, and is then applied to a well of a dot blot apparatus and the volume is suctioned through a piece of nitrocellulose. The nitrocellulose filter is then developed with the same procedure to develop Western blots, as described hereinabove in Example 9, using a monoclonal antibody recognizing a myc epitope.

Example 10

Identification of the Multimeric Polypeptide Complex from Human Tissue

A. Preparation of Tissue Extract

Cancer tissue, which has been snap frozen and stored at −70 C. is prepared for Western blot analysis. Protein extracts are prepared by homogenizing tissue samples in 0.1 M tris-HCl (pH 7.5), 15% (w/v) glycerol, 0.2 mM EDTA, 10 ug/mL leupeptin, and 1.0 mM phenylmethylsulfonylfluoride. S. R. Kain et al., Biotechniques 17: 982 (1994) Following homogenization, the homogenates are centrifuged at 4 C. for 5 minutes to separate supernatant from debris. For protein quantitation, 2–5 uL of supernate is added to 1.5 mL of Coomassie Protein Reagent (Pierce Chemical Co., Rockford, Ill.) and the absorbance is read at 595 nm.

B. Analysis of Tissue Extract

The cancer tissue extract, as described supra, is analysed by Western blot. The samples are prepared in both a reducing sample buffer (final concentration of 50 mM tris pH 6.8, 10% glycerol (v/v), 2% sodium dodecyl sulfate (w/v), 2% beta-mercaptoethanol (v/v), 0.01% bromphenol blue (w/v)) and a non-reducing sample buffer (final concentration of 50 mM tris pH 6.8, 10% glycerol (v/v), 2% sodium dodecyl sulfate (w/v), and 0.01% bromphenol blue (w/v)) and then electrophoresed on SDS-polyacrylamide gels (SDS-PAGE) using standard methods and reagents known in the art. (J. Sambrook et al., supra) Specifically, 40 μl of sample is added to 10 μl of sample buffer (5×) and the mixture is boiled for 5–10 minutes. Fifteen μl of that prepared sample is then loaded on a 10–20% tricine gel, 1 mm thick, (Novex, San Diego, Calif.) and is electrophoresed at 110 V for approximately 90 minutes. These gels are then blotted overnight at 20V onto a solid medium such as nitrocellulose, and the EU250, TU104, and BU101 protein bands are visualized using Western blotting techniques with monoclonal or polyclonal antisera recognizing EU250, TU104, or BU101. Specifically, the nitrocellulose blot is removed and blocked with 0.2% I-block® (Tropix, Bedford, Mass.) for 60 minutes at room temperature. An appropriate amount of the primary antibody is then added. The primary antibody solution is exposed to the blot for 60 minutes at room temperature with shaking. The blot is then washed three times with I-block® solution. The secondary antibody, including either biotinylated goat anti-rabbit IgG or biotinylated goat anti-mouse IgG, is then prepared in I-block® solution at an appropriate dilution (1:5000) and exposed to the blot for 60 minutes at room temperature with shaking. The blot is then washed three times with I-block® solution. The conjugate, alkaline phosphatase labeled streptavidin, is then prepared in I-block® solution at an appropriate dilution (1:10,000) and exposed to the blot for 30 minutes at room temperature with shaking. The blot is then washed three times with I-block® solution, followed by two times with assay buffer (20 mM tris (pH 9.8)/1 mM magnesium chloride). Twenty five milligrams of 5-bromo-4-chloro-3-indolyl phosphate, BCIP, is dissolved in 0.5 mL of dimethylformamide. One hundred microliters of this BCIP solution is then mixed with 30 mLs of assay buffer and this BCIP substrate solution is exposed to the blot until bands are visible. The blot is then removed from the substrate solution and allowed to dry in the air. Electronic copies of the blots are obtained by scanning the dried blot.

C. Ion Exchange Chromatography

The cancer tissue extract is purified using anion exchange chromatography. Specifically, the extract is applied to a Mono Q 5/5 column (Pharmacia) equilibrated with 20 mM piperazine, pH 6.0. The proteins are eluted using a linear gradient of sodium chloride. One hundred microliters of each fraction is boiled in the presence of 0.1% beta-mercaptoethanol and is then applied to a well of a dot blot apparatus and the volume is suctioned through a piece of nitrocellulose. The nitrocellulose filter is then developed with the same procedure to develop Western blots, as described hereinabove in Example 9, using polyclonal antisera recognizing BU101, EU250 or TU04.

D. Gel Filtration Chromatography

Semi-purified cancer tissue extract, as described supra, is further purified using gel filtration chromatography. The sample is applied to a 10 mm×30 cm column of Superose 12 (Pharmacia). The column is run with a single buffer of PBS (50 mM phosphate, 150 mM sodium chloride, pH 7.4) at a flowrate of 0.4 mL/min. The column is calibrated with molecular weight standards available from Pharmacia.

The elution of EU250, TU104, and BU101 from the Superose 12 column is monitored by immunorecognition with anti-BU101, anti-EU250, or anti-TU104 polygonal antisera. Each fraction is sampled. One hundred microliters of each fraction is boiled in the presence of 0.1% beta-mercaptoethanol and is then applied to a well of a dot blot apparatus and the volume is suctioned through a piece of nitrocellulose. The nitrocellulose filters are then developed with the same procedure to develop Western blots, as described hereinabove in Example 9, using anti-BU101, anti-EU250, or anti-TU104 polyclonal antisera.

What is claimed is:

1. A purified multimeric polypeptide antigen (MPA) comprising at least one EU250 polypeptide (SEQ ID NO:3) and at least one polypeptide selected from the group consisting of a BU101 polypeptide (SEQ ID NO:2) and a TU104 polypeptide (SEQ ID NO:10) wherein said at least one EU250 polypeptide (SEQ ID NO:3) and said at least one polypeptide selected from the group consisting of a BU101 polypeptide (SEQ ID NO:2) and a TU104 polypeptide (SEQ ID NO:10) are covalently linked by disulfide bonds.

2. The antigen of claim 1 wherein said antigen has a molecular weight of about 20 to 70 daltons.

3. The antigen of claim 2 wherein said antigen has an isoelectric point of about less than 8.

4. The antigen of claim 1 wherein said at least one BU101 polypeptide (SEQ ID NO:2) contains a polymorphism at amino acid position number 53 selected from the group consisting of proline and leucine.

5. A composition of matter comprising a multimeric polypeptide antigen, wherein said antigen comprises at least one EU250 polypeptide and at least one polypeptide selected from the group consisting of a BU101 polypeptide and a TU104 polypeptide.

6. The composition of matter of claim 5 wherein said composition further comprises at least one antibody, bound to said multimeric polypeptide antigen, wherein said antibody is specific to at least one polypeptide selected from the group consisting of a EU250 polypeptide SEQ ID NO:3, a BU101 polypeptide SEQ ID NO:2, a TU104 polypeptide, SEQ ID NO:10, and a polypeptide having an amino acid sequence selected from the group consisting of SEQUENCE ID NO:3, SEQUENCE ID NO:2 and SEQUENCE ID NO:10.

7. The composition of matter of claim 6 wherein two antibodies are present and each binds to a separate polypeptide having an amino acid sequence selected from the group consisting of SEQUENCE ID NO:3, SEQUENCE ID NO:2 and SEQUENCE ID NO:10.

8. The composition of matter of claim 7 wherein each of said two antibodies binds to a EU250 polypeptide SEQ ID NO:3.

9. The composition of matter of claim 7 wherein each of said two antibodies binds to a polypeptide selected from the group consisting of a BU101 polypeptide SEQ ID NO:2 and a TU104 polypeptide SEQ ID NO:10.

10. The composition of matter of claim 7 wherein one of said two antibodies binds to a EU250 polypeptide SEQ ID NO:3 and the other of said two antibodies binds to a polypeptide selected from the group consisting of a BU101 polypeptide SEQ ID NO:2 and a TU104 polypeptide SEQ ID NO:10.

11. The composition of matter of claim 7 wherein one of said two antibodies binds to a EU250 polypeptide SEQ ID NO:3 and the other of said two antibodies binds to a polypeptide having an amino acid sequence selected from the group consisting of SEQUENCE ID NO:3, SEQUENCE ID NO:2 and SEQUENCE ID NO:10.

12. The composition of matter of claim 7 wherein one of said two antibodies binds to a polypeptide selected from the group consisting of a BU101 polypeptide SEQ ID NO:2 and a TU104 polypeptide SEQ ID NO:10, and the other of said two antibodies binds to a polypeptide having an amino acid sequence selected from the group consisting of SEQUENCE ID NO:3, SEQUENCE ID NO:2 and SEQUENCE ID NO:10.

* * * * *